(12) United States Patent
Edelmann et al.

(10) Patent No.: US 9,994,898 B2
(45) Date of Patent: Jun. 12, 2018

(54) MATERIALS AND METHODS FOR IDENTIFYING SPINAL MUSCULAR ATROPHY CARRIERS

(75) Inventors: Lisa Edelmann, Bronx, NY (US); Robert J. Desnick, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 816 days.

(21) Appl. No.: 14/122,871

(22) PCT Filed: Jun. 7, 2012

(86) PCT No.: PCT/US2012/041406
§ 371 (c)(1),
(2), (4) Date: Feb. 24, 2014

(87) PCT Pub. No.: WO2012/170725
PCT Pub. Date: Dec. 13, 2012

(65) Prior Publication Data
US 2014/0199695 A1      Jul. 17, 2014

Related U.S. Application Data

(60) Provisional application No. 61/494,282, filed on Jun. 7, 2011.

(51) Int. Cl.
*C12Q 1/68*      (2018.01)

(52) U.S. Cl.
CPC ......... *C12Q 1/6883* (2013.01); *C12Q 1/6827* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS 7,033,752 B1    4/2006    Melki et al.

FOREIGN PATENT DOCUMENTS

WO    WO-2009/151546 A2    12/2009

OTHER PUBLICATIONS

'Molecular Analysis of SMA Patients Without Homozygous SMN1 Deletions Using a New Strategy for Identification of SMN1 Subtle Mutations' byClermont et al. (published in Human Mutation, 2004, vol. 24, pp. 417-427).*
Jordanova et al. (Neuromuscular Disorders 12 (2002) 378-385).*
Ogino et al. Human Genetics (2002) 111:477-500.*
Cusco et al. (Human Mutation 20:452-459, 2002).*
Eggerman et al. (European Journal of Human Genetics (2005)).*
Arkblad. Neuromuscular Disorders 16 (2006) 830-838 (Year: 2006).*
Chen et al., Duplications and de novo deletions of the SMNt gene demonstrated by fluorescence-based carrier testing for spinal muscular atrophy. *Am. J. Med. Genet.* 85:463-9 (1999).
Clermont et al., Molecular analysis of SMA patients without homozygous SMN1 deletions using a new strategy for identification of SMN1 subtle mutations. *Hum. Mut.* 24:417-27 (2004).
Genbank Accession No. AC139284, *Homo sapiens* chromosome 5 clone RP11-842E11, dated Jan. 29, 2003.
Genbank Accession No. NG_008691.1, *Homo sapiens* survival of motor neuron 1, telomeric (SMN1), RefSeqGene on chromosome 5, dated Oct. 11, 2008.
Genbank Accession No. NM_000344.3, *Homo sapiens* survival of motor neuron 1, telomeric (SMN1), transcript variant d, mRNA, dated Mar. 24, 1999.
Genbank Accession No. NP_000335.1, survival motor neuron protein isoform d [*Homo sapiens*], dated Mar. 24, 1999.
Genbank Accession No. NT_006713.14, *Homo sapiens* chromosome 5 genomic contig, reference assembly, dated Nov. 29, 2000.
Genbank Accession No. NT_006713.15, *Homo sapiens* chromosome 5 genomic contig, GRCh37.p13 Primary Assembly, dated Nov. 29, 2000.
Genbank Accession No. U80017, *Homo sapiens* basic transcription factor 2 p44 (btf2p44) gene, partial cds, neuronal apoptosis inhibitory protein (naip) and survival motor neuron protein (smn) genes, complete cds, dated Dec. 19, 1996.
Hendrickson et al., Differences in SMN1 allele frequencies among ethnic groups within North America. *J. Med. Genet.* 46:641-644 (2009).
International Preliminary Report on Patentability, United States Patent Office, PCT/2012/041406, dated Dec. 10, 2013.
Lefebvre et al., Identification and characterization of a spinal muscular atrophy-determining gene. *Cell* 80:155-165 (1995).
Lorson et al., A single nucleotide in the SMN gene regulates splicing and is responsible for spinal muscular atrophy. *Proc. Natl. Acad. Sci. USA* 96:6307-11 (1999).
Luo et al., An Ashkenazi Jewish SMN1 haplotype specific to duplication alleles improves pan-ethnic carrier screening for spinal muscular atrophy. *Gen. Med.* 1-8 (2013).
McKusick et al., Spinal Muscular Atrophy, Type I, Phenotype MIM# 253300 (1986).
McKusick et al., Spinal Muscular Atrophy, Type II, Phenotype MIM# 253550 (1986).

(Continued)

*Primary Examiner* — Juliet C Switzer
(74) *Attorney, Agent, or Firm* — Marshall, Gerstein & Borun LLP

(57) ABSTRACT

Materials and methods for identifying carriers of genetic determinants of spinal muscular atrophy are disclosed. In particular, polymorphisms in linkage disequilibrium are associated as markers of spinal muscular atrophy alleles detectable by various techniques, including multiplex ligation-dependent probe analysis, sequence analysis, and RFLP detection. The materials and methods of the disclosure are particularly useful in identifying silent (2+0) carriers of spinal muscular atrophy in which two copies of the SMN1 gene are located on a single human chromosome 5 and no copies of the gene are located on the chromosome 5 homolog.

8 Claims, 5 Drawing Sheets

(56) References Cited

OTHER PUBLICATIONS

McKusick et al., Spinal Muscular Atrophy, Type III, Phenotype MIM# 253400 (1986).
McKusick et al., Spinal Muscular Atrophy, Type IV, Phenotype MIM# 271150 (1986).
Morrison et al., Dinucleotide repeat polymorphism proximal to the spinal muscular atrophy region at D5S681. *Hum. Mol. Genet.* 2(10):1753 (1993).
Ogino et al., Genetic testing and risk assessment for spinal muscular atrophy (SMA). *Hum. Genet.* 111:477-500 (2002).
Ogino et al., New insights on the evolution of the SMN1 and SMN2 region: simulation and meta-analysis for allele and haplotype frequency calculations. *J. Hum. Genet.* 12:1015-23 (2004).
Pearn, Incidence, prevalence, and gene frequency studies of chronic childhood spinal muscular atrophy. *J. Med. Genet.* 15:409-13 (1978).
Scheffer et al., Best practice guidelines for molecular analysis in spinal muscular atrophy. *Eur. J. Hum. Genet.* 9:484-91 (2001).
Soares et al., Refinement of the spinal muscular atrophy locus to the interval between D5S435 and MAP1 B. *Genomics* 15(2):365-71 (1993).
Velasco et al., Isolation of microsatellites from the spinal muscular atrophy (SMA) candidate region on chromosome 5q and linkage analysis in Spanish SMA families. *Eur. J. Hum. Genet*, 3(2):96-101 (1995).
Wirth et al., Quantitative analysis of survival motor neuron copies: identification of subtle SMN1 mutations in patients with spinal muscular atrophy, genotype-phenotype correlation, and implications for genetic counseling. *Am. J. Hum. Genet.* 64:1340-56 (1999).

\* cited by examiner

MATERIALS AND METHODS FOR IDENTIFYING SPINAL MUSCULAR ATROPHY CARRIERS

FIELD

The disclosed technology generally relates to the field of genetic counseling and, more particularly, to methods of identifying carriers of genetic determinants associated with deleterious conditions.

BACKGROUND

Spinal muscular atrophy is one of the most common and severe autosomal recessive diseases with an overall incidence of about 1 in 6,000 to 10,000 live births and a carrier frequency of 1 in 35 to 1 in 117, depending on ethnicity. The disease is characterized by the progressive degeneration and loss of anterior horn cells in the spinal cord and brain stem nuclei causing symmetric muscle weakness and atrophy, and the clinical subtypes are primarily based on age at onset. Type I disease (Werdnig-Hoffmann disease, MIM#253300), which occurs in 60-70% of patients, is characterized by onset of respiratory insufficiency at birth or before six months of age leading to death within two years. Type I patients never sit or walk. Onset of Type II disease (MIM#253550) typically occurs after 6 months of age; these infants can sit, but never walk unaided, and have significantly reduced life expectancy. Patients with Type III disease (Kugelberg-Welander syndrome, MIM#253400) present after 18 months of age, stand and walk, but often become wheelchair-bound during childhood or early adulthood. Type IV disease (MIM#271150) is characterized by adult onset (mean age of 35 years) and slow disease progression.

Homozygous mutations of the SMN1 gene on chromosome 5q13.2 are the major cause of SMA (Lefebvre et al., Cell 80:155-165, 1995). In approximately 95-98% of SMA patients, both copies of SMN1 exons 7 and 8 are either deleted or are rendered non-functional due to gene conversion of SMN1 to SMN2 (Ogino et al., J. Hum. Genet. 12:1015-1023 (2004)). The remaining 2-5% of patients are compound heterozygotes that carry an intragenic mutation(s) on one allele and either a deletion or gene conversion mutation on the other allele (Wirth et al., Am J. Hum. Genet. 64:1340-1356, 1999). SMN1 and SMN2 are separated by approximately 1.4 Megabases and comprise the telomeric and centromeric members, respectively, of a set of genes, including NAIP, present within a segmental duplication on 5q13.2. The SMN1 (NCBI Reference Sequence NG_008691) and SMN2 genes have high sequence similarity even in the promoter regions and there are no encoded amino acid differences. A single base change affecting a putative splice enhancer in exon 7 (840C>T; position 27006 of SEQ ID NO:1), however, accounts for splicing differences such that the majority of SMN2 transcripts lack exon 7 (Lorson et al., Proc. Natl. Acad. Sci. (USA) 96:6307-6311 (1999)). Although some genotype/phenotype correlations have been established among patients that carry SMN1 point mutations, the presence of additional copies of SMN2 positively modifies clinical prognosis (Wirth et al., 1999).

The majority of mutations causing all four SMA types (i.e., Types I-IV) involve SMN copy number loss. Mutation detection typically involves PCR amplification of SMN1 exon 7, which is homozygously absent in most affected individuals. Carrier screening, however, is performed by dosage-sensitive but location-insensitive methods that can distinguish SMN1 and SMN2, but that provide no information on gene location. These carrier screens are currently performed using quantitative PCR (qPCR), Multiplex Ligation-Dependent Probe Amplification (MLPA), and/or Taqman quantitative technology. These methods cannot determine the number of SMN1 copies present on individual chromosomes. Given the tight linkage of the structurally related SMN1 and SMN2 genes and the opportunity for gene conversion as well as gene duplication or deletion, it is unsurprising that these methods exhibit detectability varying from 71-94% due to the inability to identify individuals that are SMA silent carriers, such as silent (2+0) carriers. Information on gene location is urgently needed to allow genetic counseling to consider the effects of segregation in germ cell production and its implications for offspring. Individuals with two SMN1 copies on one chromosome (a duplication allele) and no copies on the other (a deletion allele), are referred to as silent (2+0) carriers, as most individuals with two intact SMN1 copies, one copy on each chromosome (1+1), are not carriers (FIG. 1). Thus, SMA carrier detection by current techniques that are location-insensitive generates false negative results.

The frequency of silent (2+0) carriers varies based on ethnicity and is directly proportional to the product of the frequency of deletion and duplication alleles in a given population. Among Ashkenazi Jews, the SMA carrier frequency has been reported at 1 in 41 with a detectability of approximately 90%. Of the remaining 10%, about 8% are silent (2+0) carriers and the rest carry intragenic mutations. The frequency of SMN1 silent (2+0) carriers in any population modifies the risk of being a carrier after a negative screening result. For example, in the African American (AA) population, the frequency of duplication (2+1) individuals is relatively high (47%), and consequently there are more silent (2+0) carriers, such that the carrier detection rate is only 71% with a residual risk of 1 in 121 after a negative result.

Accordingly, a need exists in the art for screening methods for SMA and SMA carriers that are location-sensitive in addition to being sensitive to copy number, e.g., copy numbers of SMN1 and/or SMN2 alleles. An accurate assessment of the risk of producing offspring with SMA requires knowledge of both the copy numbers of SMN1 and/or SMN2 and of the location of those alleles that are found in a given genome. Such information is vital to competent genetic counseling of prospective parents.

SUMMARY

The technology disclosed herein solves at least one of the aforementioned problems in the art. More specifically, the disclosure provides methods of identifying carriers of SMA, such as silent SMA carriers, as exemplified by silent (2+0) carriers of SMA. The ability to identify silent (2+0) carriers would significantly improve carrier detection and, therefore, efforts were directed to identifying ethnic-specific SMN1 founder deletion and/or duplication alleles by detecting a genotype unique to either the deletion or duplication alleles present in silent (2+0) carriers.

The disclosure provides AJ founder alleles for SMN1, including one that is present in approximately half of all AJ SMN1 duplication (2+1) individuals. This duplication haplotype can be identified by two tightly linked, highly specific polymorphisms in SMN1 (SEQ ID NO:1), g.27134T>G (position 27134 of SEQ ID NO:1) in intron 7 and g.27706_27707 delAT (positions 27706 and 27707 of SEQ ID NO:1) in exon 8. These polymorphisms, and other genetic features noted in this disclosure, bear the numbering used for the reference SMN1 sequence submitted to Genbank under Accession No. NG_008691.1 (cognate mRNA reference sequence NM_000344.3; encoded amino acid reference sequence NP_000335.1), all incorporated herein by reference in their entireties. These polymorphisms can be used in conjunction with dosage-sensitive methods to detect silent (2+0) carriers and improve the overall carrier detection rate in a particular ethnic group, such as the Ashkenazi Jewish group, and in other ethnic or racial groups, such as Caucasians, Asians, African-Americans and Hispanics. For example, either or both of these polymorphisms can be detected using any known technique, including but not limited to, probe hybridization under stringent conditions, wherein the probe sequence is perfectly complementary to a sequence including the polymorphic site, a PCR amplification coupled to sequence analysis, restriction fragment length polymorphism, and the like. In view of the polymorphisms disclosed herein, moreover, it is contemplated that these relative hotspots might yield other forms of localized nucleic acid sequence changes, such as deletions of 1-5 or 1-10 nucleotides, insertions of 1-5 or 1-10 nucleotides and substitutions at position 27134 of SEQ ID NO:1 wherein any conventional nucleotide replaces the wild type T/U and/or the wild type AT at positions 27706-27707 of SEQ ID NO:1.

Particular aspects of the disclosure are described in the following enumerated paragraphs.

1. A method of identifying a human subject as a carrier of a SMN1 duplication allele comprising:
   (a) obtaining a nucleic acid sample from a human subject;
   (b) screening the nucleic acid by determining
      (i) the identity of the nucleotide corresponding to position 11678 of SEQ ID NO:1; or
      (ii) the identity of the nucleotide corresponding to position 15774 of SEQ ID NO:1; or
      (iii) the identity of the nucleotide corresponding to position 22804 of SEQ ID NO:1; or
      (iv) the identity of the nucleotide corresponding to position 26190 of SEQ ID NO:1; or
      (v) the identity of the nucleotide corresponding to position 27134 of SEQ ID NO:1, or
      (vi) whether the A-T dinucleotide corresponding to positions 27706-27707 of SEQ ID NO:1 has been deleted; and
   (c) identifying the human subject as a carrier of a SMN1 duplication allele if
      (i) the nucleotide corresponding to position 11678 of SEQ ID NO:1 is not G or there is a nucleotide inserted between nucleotides corresponding to positions 11678 and 11679 of SEQ ID NO:1;
      (ii) the nucleotide corresponding to position 15774 of SEQ ID NO:1 is not G or there is a nucleotide inserted between nucleotides corresponding to positions 15774 and 15775 of SEQ ID NO:1;
      (iii) the nucleotide corresponding to position 22804 of SEQ ID NO:1 is not G or there is a nucleotide inserted between nucleotides corresponding to positions 22804 and 22805 of SEQ ID NO:1;
      (iv) the nucleotide corresponding to position 26190 of SEQ ID NO:1 is not A or there is a nucleotide inserted between nucleotides corresponding to positions 26190 and 26191 of SEQ ID NO:1;
      (v) the nucleotide corresponding to position 27134 of SEQ ID NO:1 is not a T or there is at least one nucleotide inserted between nucleotides corresponding to positions 27134 and 27125 of SEQ ID NO:1; or
      (vi) the A-T dinucleotide corresponding to positions 27706-27707 of SEQ ID NO:1 is deleted.

2. The method according to paragraph 1 wherein the human subject is identified as a carrier of a SMN1 duplication allele based on the presence of a nucleotide structure selected from the group consisting of a T corresponding to the nucleotide at position 11678 or 11679 of SEQ ID NO:1, an A corresponding to the nucleotide at position 15774 or 15775 of SEQ ID NO:1, an A corresponding to position 22804 or 22805 of SEQ ID NO:1, a G corresponding to the nucleotide at position 26190 or 26191 of SEQ ID NO:1, a G corresponding to the nucleotide at position 27134 or 27135 of SEQ ID NO:1 and an AT deletion corresponding to the nucleotides at positions 27706-27707 of SEQ ID NO:1.

3. A method of identifying a human Spinal Muscular Atrophy (SMA) silent (2+0) carrier comprising:
   (a) screening nucleic acid from a human subject by determining
      (i) the identity of the nucleotide corresponding to position 27134 of SEQ ID NO:1, or
      (ii) whether the A-T dinucleotide corresponding to positions 27706-27707 of SEQ ID NO:1 has been deleted; and
   (b) identifying an individual as a silent (2+0) carrier of SMA if the nucleotide corresponding to position 27134 of SEQ ID NO:1 is not a T or the A-T dinucleotide corresponding to positions 27706-27707 of SEQ ID NO:1 is deleted, or both.

4. The method according to paragraph 3 further comprising obtaining a sample of nucleic acid from the human subject.

5. The method according to paragraph 3 or 4 further comprising providing genetic counseling to the human subject based on the results of the method of identifying a human Spinal Muscular Atrophy (SMA) silent (2+0) carrier.

6. A method of identifying a human Spinal Muscular Atrophy (SMA) silent (2+0) carrier comprising:
   (a) screening nucleic acid from a human subject by determining the identity of the nucleotide corresponding to position 27134 of SEQ ID NO:1;
   (b) further determining if the A-T dinucleotide corresponding to positions 27706-27707 of SEQ ID NO:1 has been deleted; and
   (c) identifying an individual as a silent (2+0) carrier of SMA if the nucleotide corresponding to position 27134 of SEQ ID NO:1 is G and the A-T dinucleotide corresponding to positions 27706-27707 of SEQ ID NO:1 is deleted.

7. The method according to paragraph 6 further comprising obtaining a sample of nucleic acid from the human subject.

8. The method according to paragraph 6 or 7 further comprising providing genetic counseling to the human subject based on the results of the method of identifying a human Spinal Muscular Atrophy (SMA) silent (2+0) carrier.

9. The method according to paragraph 6 or 7 wherein the identity of the nucleotide corresponding to position 27134 of SEQ ID NO:1, and the identities of the nucleotides corresponding to positions 27706 and 27707 of SEQ ID NO:1 are determined by restriction fragment length polymorphism.

10. The method according to paragraph 6 or 7 wherein a G is identified at the position corresponding to position 27134 of SEQ ID NO:1 by restriction fragment length polymorphism using restriction endonuclease HpyCH4III.

11. A method of identifying a human Spinal Muscular Atrophy (SMA) silent carrier comprising screening the nucleic acid from a human subject for a SMN1 (SEQ ID NO:1) haplotype that correlates with SMN1 deletion and increased occurrence of SMA in a human population, wherein the SMA haplotype comprises:

(i) a polymorphism selected from the group consisting of D5S681 having allele 2, D5S435 having allele 1 or allele 5, MS1 having allele 4, and D5S610 having allele 5, wherein the presence of the SMN1 haplotype in the nucleic acid identifies the subject as having an SMN1 deletion and being an SMA silent carrier, and wherein the absence of the SMN1 haplotype in the nucleic acid identifies the subject as not being an SMA silent carrier.

12. The method according to paragraph 11 further comprising obtaining a sample of nucleic acid from the human subject.

13. The method according to paragraph 11 or 12 wherein the silent carrier is a silent (2+0) carrier.

14. The method according to paragraph 13 further comprising providing genetic counseling to the human subject based on the results of the method of identifying a human Spinal Muscular Atrophy (SMA) silent carrier.

15. The method according to paragraph 13 wherein the SMA haplotype for D5S681-D5S435-MS1-D5S610 is 2-5-4-5.

16. The method according to paragraph 13 wherein the SMA haplotype for D5S681-D5S435-MS1-D5S610 is 2-1-4-5.

17. A method of identifying a human Spinal Muscular Atrophy (SMA) carrier comprising: screening the nucleic acid from the human subject for a SMN1 (SEQ ID NO:1) haplotype that correlates with SMN1 deletion and increased occurrence of SMA in a human population, wherein the SMA haplotype comprises polymorphism MS1 having allele 6.

18. The method according to paragraph 17 further comprising obtaining a sample of nucleic acid from the human subject.

19. A method of identifying a human Spinal Muscular Atrophy (SMA) carrier comprising: screening the nucleic acid from the human subject for a SMN1 (SEQ ID NO:1) haplotype that correlates with SMN1 duplication and increased occurrence of SMA in a human population, wherein the SMA haplotype is selected from the group consisting of (i) polymorphism D5S681 having allele 2, D5S435 having allele 5, MS1 having allele 4, and D5S610 having allele 5;
(ii) polymorphism D5S681 having allele 2; D5S435 having allele 5, MS1 having allele 9, and D5S610 having allele 4;
(iii) polymorphism D5S681 having allele 2, D5S435 having allele 5, MS1 having allele 6; and
(iv) polymorphism D5S681 having allele 2, D5S435 having allele 5, MS1 having allele 6, and D5S610 having allele 10,
wherein the presence of the SMN1 haplotype in the nucleic acid identifies the subject as having an SMN1 duplication and being an SMA carrier, and wherein the absence of the SMN1 haplotype in the nucleic acid identifies the subject as not being an SMA carrier.

20. The method according to paragraph 19 further comprising obtaining a sample of nucleic acid from the human subject.

21. An isolated nucleic acid comprising a sequence selected from the group consisting of sequences of at least 17 nucleotides comprising a nucleotide corresponding to position 27134 of SEQ ID NO:1, sequences of at least 17 nucleotides comprising a dinucleotide corresponding to position 27705 and 27708 of SEQ ID NO:1, sequences of at least 17 nucleotides comprising the sequence set forth at positions 69-148 of SEQ ID NO:2, sequences of at least 17 nucleotides comprising the sequence set forth at positions 61-127 of SEQ ID NO:3, and sequences of at least 17 nucleotides comprising the sequence set forth at positions 61-216 of SEQ ID NO:4.

22. The isolated nucleic acid according to paragraph 21 wherein the nucleic acid is about 10 to 200 nucleotides in length.

23. A kit for diagnosing a Spinal Muscular Atrophy (SMA) carrier comprising the isolated nucleic acid according to paragraph 21 and a protocol for the use thereof in diagnosis of a SMA carrier.

Other features and advantages of the present disclosure will become apparent from the following detailed description, including the drawing. It should be understood, however, that the detailed description and the specific examples, while indicating preferred embodiments, are provided for illustration only, because various changes and modifications within the spirit and scope of the invention will become apparent to those skilled in the art from the detailed description.

DETAILED DESCRIPTION

Figure 1:
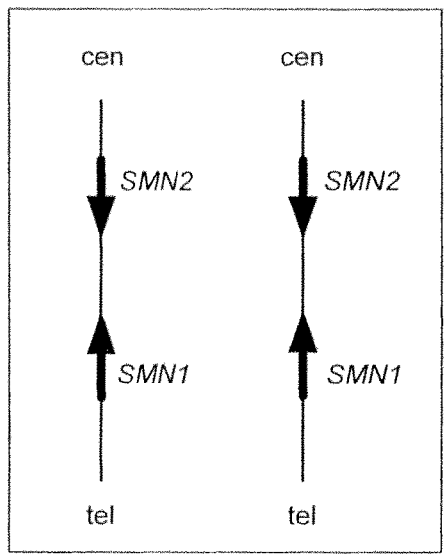
FIG. 1. A schematic of SMN1 and SMN2 alleles on chromosome 5q13 is provided. (A) Wild-type with one copy of SMN1 and SMN2 on each chromosome 5 (1+1) (B) SMA carrier with one copy of SMN1 on one chromosome 5 and loss of SMN1 on the other chromosome (1+0). (C) Duplication with two copies of SMN1 one on one chromosome 5 and one copy on the other chromosome (2+1) (D) SMA silent carrier with two copies of SMN1 on one chromosome 5 and loss of SMN1 on the other chromosome (2+0).
Figure 1:
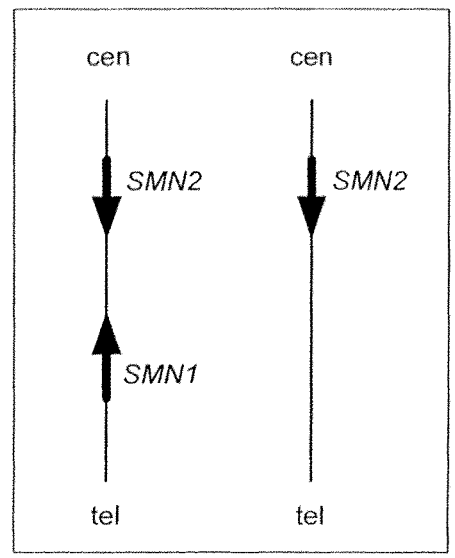
Figure 1:
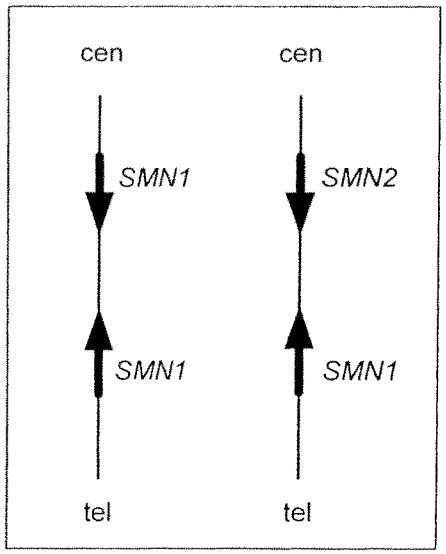
Figure 1:
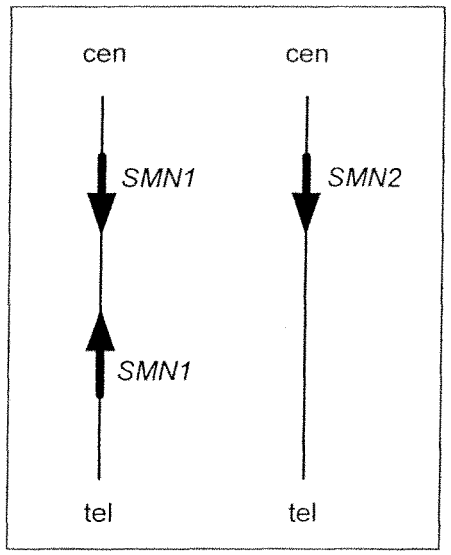

Spinal Muscular Atrophy (SMA) is the most common lethal inherited disease in children. Approximately 94% of affected human individuals show a bi-allelic loss of SMN1 exon 7, and such losses are known to be the result of intragenic point mutations altering splicing patterns of SMN1 mRNA, intragenic deletions eliminating at least part of exon 7 as well as loss of the SMN1 coding region via deletion. Disposed on human chromosome 5 is SMN1 (SEQ ID NO:1) and SMN2 (differing from the sequence of SMN1 set forth in SEQ ID NO:1 by C>T at position 27006 of SEQ ID NO:1). These two genes are highly homologous, with a telomeric relative location for SMN1 and a centromeric relative location for SMN2. The SMN2 gene sequence differs from the SMN1 sequence in exon 7 due to a point mutation, and this difference alone is sufficient to result in SMA. Given the relative proximity of SMN1 and SMN2, and given the presence of repeats in this localized region of chromosome 5 (i.e., 5q13.2), the genetics of SMA become complicated by the possibility of gene conversion as well as duplications and/or deletions. Although current methodologies can identify individual mutations in terms of sequence variation and can even provide a measure of SMN1 copy number, these methods cannot discriminate beyond copy number to identify SMA carriers having, for example, excessive copies of the SMN1 gene on one chromosome and no copies of SMN1 on the other chromosome. In particular examples, the wild-type copy number of two for SMN1 is present in the genome of SMA carriers because of an imbalance of SMN1 on the chromosome 5 homologs (i.e., both copies of SMN1 on one member of the chromosome 5 pair). The disclosure advances efforts to identify SMA carriers by providing methods of identifying silent carriers of Spinal Muscular Atrophy (SMA) that contain a chromosomally unbalanced load of SMN1, such as the silent (2+0) carriers of SMA.

To aid in understanding the detailed description of the compositions and methods according to the disclosure, a few express definitions are provided to facilitate an unambiguous disclosure of the various aspects of the disclosure.

A "polymorphism" is a difference in DNA or RNA sequence among individuals, groups, or populations that gives rise to different alleles. The alleles may be alleles of a gene encoding a gene product, such as SMN1, and the polymorphism may involve a sequence change (relative to wild type sequence) in the coding region, in the transcribed but untranslated region associated with a gene, in the expression control region of a gene, in the proximal nucleic acid environment of a gene or located at some distance from the gene. Typically, polymorphisms of interest in identifying SMA carriers will be genetically linked to the SMN1 gene. Exemplary polymorphisms include substitutions of one or more (e.g., 2, 3, 4, 5, 6, 7, 8, 9, 10, or more) nucleotides, deletions of a polynucleotide region comprising at least 1, 2, 3, 4, 5, 6, 7, 8, 9, 10, 15, 20, 25, 30, 40, 50, 75, 100, 150, 200, 250, 500, 1,000, or more nucleotides, and insertions of nucleotides into a polynucleotide region wherein the insertion is of a length defined above in the context of addressing deletions.

A "SNP" is a single-nucleotide polymorphism, or single nucleotide difference in the nucleic acid sequence relative to the wild type sequence.

As used herein, a "haplotype" is a partial genotype of at least one determinant containing at least one polymorphism, such as single-nucleotide polymorphism (SNP), a deletion or an insertion, on a chromosome. For haplotypes comprising more than one polymorphism, the individual polymorphisms exhibit statistically significant linkage disequilibrium. Exemplary polymorphisms are single- or multiple-nucleotide substitutions, insertions or deletions and each polymorphism may be localized to a determinant that is a gene recognized in the art, such as SMN1, a new gene, or an extragenic region of a chromosome.

"Copy number" refers to the number of physical copies of a genetic determinant, such as a gene, or region of the genome of an organism.

A "carrier" or genetic "carrier" is an individual containing at least one copy of an allele of a genetic determinant that is involved in elaborating a given phenotype, such as SMA, provided that the individual containing the copy or copies of the determinant does not exhibit the phenotype.

A "silent carrier" is a carrier that cannot be detected using a copy number-based diagnostic technique conventional in the art.

SMA is a pan-ethnic disease, and the frequency of single SMN1 exon 7 copy number in various ethnic groups are known. In particular, the single-copy exon 7 genotype frequencies range from 2.7% (1 in 37) in the Caucasian population, 2.2% (1 in 46) in the Ashkenazi Jewish population, 1.8% (1 in 56) in the Asian population, 1.1% (1 in 92) in the African American population, down to 0.8% (1 in 125) in the Hispanic population. Hendrickson et al., J. Med. Genet. 46:641-644 (2009), incorporated herein by reference in its entirety. Thus, the disclosure is not limited to the exemplified application of identifying carriers in the Ashkenazi Jewish population, but rather extends to identification of SMA carriers such as silent (2+0) SMA carriers in any ethnic population, including the populations characterized herein.

Identification of deletion/duplication founder alleles provides a general approach to identify silent carriers and improve carrier detection in various ethnic/racial groups, as exemplified by the data disclosed herein that relates to the Ashkenazi Jewish (AJ) population. The data identify founder alleles in the Ashkenazi Jewish (AJ) population. Carrier screening of 692 healthy AJ adults was conducted by Multiplex Ligation-dependent Probe Analysis (MLPA), which identified 1 in 46 (2.2%) deletion (1+0) carriers, and 1 in 7 duplication (2+1) individuals. These data indicate that carrier detectability using only SMN1 gene dosage in this population is around 90%. Microsatellite analyses of markers flanking the SMA locus identified two deletion haplotypes and one major duplication founder haplotype. Importantly, two polymorphisms tightly linked to SMN1, i.e., g.27134T>G in intron 7 (position 27006 of SEQ ID NO:1, see Genbank Acc. No. NG_008691.1) and g.27706_27707 delAT in exon 8 (positions 27706-27707 of SEQ ID NO:1, see Genbank Acc. No. NG_008691.1), were detected on the major AJ duplication allele, but not in 351 AJ individuals with two SMN1 copies, making the haplotype highly specific for duplication alleles and effectively increasing the accuracy of carrier detection. It is expected that the greatest diagnostic accuracy will be obtained when assaying for both of the above-identified polymorphisms, but the disclosure comprehends diagnostic methods assaying for either polymorphism alone or in conjunction with one or more other polymorphisms. Identification of specific markers for duplication or deletion alleles is expected to improve carrier detectability and decrease the current residual risk due to the inability to detect silent (2+0) carriers in any population.

In 2008, The American College of Medical Genetics (ACMG) recommended offering carrier screening for SMA to all couples regardless of race or ethnicity. Preconceptual genetic counseling for SMA is complicated by the nature of the mutations, which involve copy number loss of SMN1 by deletion or gene conversion with the highly homologous, centromeric copy, SMN2, as well as the high rate of de novo mutations at the locus. Since most mutations involve copy number loss, carrier detectability is limited by the false negative rate that varies from 4% to 27%, based on ethnicity, due to the inability to detect silent (2+0) carriers with two copies of SMN1 on one chromosome and none on the other.

To overcome this limitation, and to increase the detectability of SMA carriers in the AJ population, founder alleles with unique polymorphisms were sought to distinguish the silent (2+0) carriers from wild-type (1+1) individuals. Screening of 692 AJ individuals by MLPA established the frequencies of normal, deleted, and duplicated SMN1 alleles and identified deletion (1+0) and duplication (2+1) individuals to seek unique deletion- and/or duplication-allele haplotypes surrounding the SMN1 locus. Haplotype studies of the AJ population were aided by the availability of founder mutations identified in shared haplotype blocks, which facilitated carrier detection for recessive disorders prevalent among AJ individuals.

To search for potential founder alleles, microsatellite analyses were performed with markers that flanked the SMN1 locus and marker trait association studies were performed with four of the most tightly linked markers (D5S681-D5S435-MS1-D5S610; SEQ ID NOS:5, 6, 2, and 7, respectively), as described in the following examples. D5S681 was reported in Morrison et al., Hum Mol Genet. 2(10):1753 (1993); Soares et al., Genomics. 15(2):365-71 (1993) reported D5S435; for D5S610, see Velasco et al., Eur J Hum Genet. 3(2):96-101 (1995). MS1 is a newly identified microsatellite marker, as are MS2 (SEQ ID NO:3) and MS3 (SEQ ID NO:4). Microsatellites are also called simple sequence repeats, and constitute a class of genetic polymorphisms commonly used for mapping, linkage analysis and the tracing of inheritance patterns. Typically, microsatellites are tandemly repeated sequences. The number of times the unit is repeated in a given microsatellite can be highly variable, a characteristic that makes them useful as genetic markers.

A comparison of the haplotype frequencies in deletion (1+0) and duplication (2+1) individuals to those in AJ non-carrier controls identified two deletion- and three duplication-specific haplotypes with p values≤0.001 (Table 3). Of these haplotypes, one was present in approximately 46.4% (32/69) of the duplication alleles tested, but was absent in all 78 AJ control individuals making it highly specific.

The following examples illustrate embodiments of the disclosure. Example 1 discloses materials and methods used in the studies disclosed herein. Example 2 provides the results of genetic screening of the AJ population for deletions and insertions associated with SMN1, along with a determination of the frequency of silent (2+0) carriers of SMN1 mutations associated with SMA. Disclosed in Example 3 is the results of genetic analyses of the deletion (1+0) and duplication (2+1) mutation groups in the AJ population. Example 4 discloses haplotype reconstruction in individuals with deletions (1+0) or duplications (2+1). Example 5 describes the sequencing of the major duplication allele in the AJ population, identification of an additional two polymorphisms, and characterization of these polymorphisms in several human populations. Example 6 provides the results of RFLP analyses based on the g.27134T>G SNP from SMN1 exon 7. Example 7 discloses data and analyses thereof that establish the improved identification of SMA carriers, e.g., SMA silent (2+0) carriers, in various racial and ethnic groups.

Example 1

Specimen Collection and DNA Isolation

Genomic DNA was obtained with informed consent from the peripheral blood specimens of anonymous individuals of Ashkenazi Jewish, African American, Hispanic and European ancestry living in the Greater New York Metropolitan area. DNA was isolated using the Puregene® DNA Purification kit (Qiagen, Valencia, Calif.) according to the manufacturer's instructions.

Multiplex Ligation-Dependent Probe Amplification (MLPA)

A total of 200 ng of genomic DNA from each specimen was used for multiplex ligation-dependent probe analysis (MLPA) analysis with the Salsa MLPA SMA P021 kit (MRC-Holland, Amsterdam, Netherlands) according to the manufacturer's instructions. The MLPA PCR products were separated by capillary electrophoresis using the ABI-3130XL Genetic Analyzer (Applied Biosystems Inc, Foster City, Calif.). The results were imported as html files into GeneMarker software (Softgenetics, LLC., State College, Pa.) for MLPA data analysis using population normalization with the MLPA ratio as the analysis method and peak height as the quantification method. The peak-heights for each of the 38 MLPA probe ligation products in the test sample were compared to the mean peak-heights of at least three normal controls, and the test/wild-type peak-height ratios for each probe ligation product were determined. The peak-height ratios less than 0.8 and/or greater than 1.3 would indicate the loss or gain of the copy number for each probe, respectively.

Microsatellite Analysis

Microsatellite analysis was performed with previously described markers, D5S681, D5S435, D5S610 that flank the SMN1 and SMN2 genes on 5q13 (Scheffer et al., Eur. J. Hum. Genet. 9:484-494 (2001)). Three novel markers, MS1 (SEQ ID NO:2), MS2 (SEQ ID NO:3) and MS3 (SEQ ID NO:4), were based on publicly available human genomic sequence using the UCSC genome database. The following primer pairs were designed to amplify MS1: MS1F (5'-TAAATGTCAAATTTATGTATGGG-3'; SEQ ID NO:12) and MS1R (5'-CTGTGATTGAAAC AAAGACACCT-3'; SEQ ID NO:13); MS2: MS2F (5'-TCCATGGATACGGA-GAGCTG-3'; SEQ ID NO.:16) and MS2R (5'-TGATG-GCACCACAACCATGC-3'; SEQ ID NO.:17) and MS3: MS3F (5'-TCAGGA CCCTCCTCATCATC-3'; SEQ ID NO.:18) and MS3R (5'-CGGGATCTCTTCTCCACAGA-3'; SEQ ID NO.:19). All forward primers were 6-carboxy Fluorescein-labeled or 6-FAM-labeled (Invitrogen). Each primer pair was amplified separately in a total volume of 25 µl using 200 ng of genome DNA, 1×PCR buffer (Invitrogen), 1.5 mM $MgCl_2$, 0.3 µM forward and reverse primers and 0.3 µl of platinum Taq polymerase (Invitrogen). The amplifications were initiated with 10 minutes at 94° C., followed by 35 cycles of 30 seconds at 94° C., 30 seconds at 58° C. and 30 seconds at 72° C., with a final extension for 10 minutes at 72° C. PCR products were diluted 1:10 and run on an ABI 3730 DNA analyzer (Applied Biosystems) and the results were analyzed with GeneMapper software v3.7 (Applied Biosystems).

LongRange PCR and Sequencing

Long-range PCR spanning the fragment between exon 7 and exon 8 (1025 bp) of the SMN1 gene in AJ individuals identified with three copies of the SMN1 gene by MLPA was performed using LongRange PCR reagents (Qiagen) with primers SMN1-E7F (5'-TCCTTTATTTTCCTTACA-GGGTTTC-3'; SEQ ID NO.:20) and SMN1-E8R (5'-CAAT-GAACAG CCATGTCCAC-3'; SEQ ID NO.:21). Primer SMN1-E7F was designed to preferentially amplify SMN1 by the inclusion of c.840C of Exon 7 at the 3' end. PCR amplification was performed according to the manufacturer's instructions in 50 µl of reaction mixture containing 500 mM dNTP, 1×PCR buffer, 2.5 mM MgCl$_2$, 2 units (U) of long-range enzyme, 400 nM of each primer, and 250 ng of purified DNA. After 3 minutes of initial denaturation at 93° C., 35 cycles of amplification were performed as follows: 15 seconds at 93° C., 30 seconds at 59° C., and 1.5 minutes at 68° C.

The PCR amplicons were purified using QIAquick PCR Purification Kit (Qiagen). The fragment was sequenced using the BigDye Terminator v1.1 Cycle Sequencing Kit (Applied Biosystems) and the products were run on the ABI 3730 automated sequencer (Applied Biosystems). The same primers used for PCR amplification were also used in the sequencing reactions. Additional primers SMN1-I7F2 (5'-AGGAAATGC TGGCATAGAGC-3'; SEQ ID NO.:22) and SMN-E8Ra (5'-CTGCTCTATGCCAGCATTTC-3'; SEQ ID NO.:23) were designed to confirm sequencing results in both directions. Sequence traces were analyzed using both Mutation Surveyor software v3.01 (SoftGenetics) and Sequencher™ version 4.8 (Gene Codes, Ann Arbor, Mich.) and by visual inspection.

TA Cloning

LongRange PCR fragments (1025 bp) from five AJ major duplication (2+1) alleles (see below) were subjected to TA-cloning. In brief, amplicons were gel-purified (Qiagen) and cloned into the PCR vector from the TOPO TA Cloning® Kit (Invitrogen) according to the manufacturer's instructions. Twelve clones from each of these duplication carrier individuals were isolated for PCR screening. Clones with the expected insert size (1025 bp) were subsequently sub-cultured, and plasmids were purified using the QIAprep Spin Miniprep Kit (Qiagen) and sequenced as described above using M13 primers (Fisher Scientific, Pittsburgh, Pa.).

Restriction Fragment Length Polymorphism Analysis (RFLP)

PCR reactions were performed to amplify a 372 bp fragment containing the g.27134T>G single nucleotide alteration with the primers SMN1-E7F (above) and SMN1-I7R1 (5' AAAAGTCTGCTGGTCTGCCTAC-3'; SEQ ID NO.:24). The amplification was carried out in a 25 µl reaction mixture with 400 nM of each primer, 200 µM dNTP, 1.5 mM MgCl$_2$ and 1 U of Platinum®Taq DNA Polymerase (Invitrogen, Carlsbad, Calif.). Cycling conditions were as follows: 94° C. for 5 minutes, followed by 30 cycles of 94° C. for 30 seconds, 59° C. for 30 seconds, 72° C. for 1 minutes and a final extension of 72° C. for 10 minutes. The g.27134T>G single nucleotide alteration resulted in a gain of a restriction site for enzyme HypCH4III. Following amplification, 5 µl of PCR product were digested with 4 U of HypCH4III (New England Biolabs, Ipswich, Mass.) at 37° C. for 4 hours and were resolved by either 6% polyacrylamide or 1.5% agarose gel electrophoresis, visualized with a UV transilluminator and photographed.

Statistical Analysis

Genotype frequencies for each microsatellite marker were tested for Hardy-Weinberg equilibrium (HWE) using the $\chi^2$ test. Haplotypes of the markers, D5S681-D5S435-MS1-D5S610, were estimated for AJ controls and AJ SMN1 deletion (1+0), duplication (2+1), and silent (2+0) carriers using SAS/Genetics version 9.2. Lengths of the various alleles for each microsatellite marker are provided in Table 8. Putative haplotypes were inferred from their frequency among all examined individuals and reconstructed based on the most likely combination of alleles. Differences in haplotype frequencies between AJ control cohort versus the AJ cohort of individuals with SMN1 deletion or duplication were tested using the $\chi^2$ test. P-values for overall and pair-wise comparisons were calculated for the four marker haplotypes with the threshold of 0.05 considered statistically significant. Improvement in the detection rate with the addition of new markers was estimated using the Bayesian approach.

Example 2

AJ Population Screening for SMN1 Deletions and Duplications

To determine the frequency of SMA deletion (1+0) and duplication (2+1) individuals in the AJ population, 692 individuals of 100% AJ ancestry (with four AJ grandparents) were screened by an SMN1- and SMN2-specific MLPA assay, which detects the copy number of 38 different genomic regions in a single reaction. Specifically, this assay determined the individual SMN1 and SMN2 exon 7 and exon 8 copy numbers for each of SMN1 and SMN2 as well as the combined SMN1 and SMN2 copy number of their respective exons 1, 4, 6 and 8. Fifteen SMN1 deletion (1+0) carriers (1 in 46 or 2.1%) were identified, which is similar to the frequency reported in other European populations. However, 99 SMN1 duplication (2+1) individuals (1 in 7 or 14%) were identified, which is twice the frequency in Europeans. No individuals with four SMN1 copies (i.e., two duplication alleles, 2+2) were identified, although the expected frequency of (2+2) individuals was 0.5% (Table 2). The observed frequencies did not deviate significantly from Hardy-Weinberg equilibrium (HWE) (exact p>0.05) and are shown in Table 1 along with the expected frequencies.

Frequency of AJ Silent (2+0) Carriers

Using the frequency of deletions (1+0) (2.2%) and duplications (2+1) (14.3%), assuming Hardy-Weinberg Equilibrium for each of three alleles (SMN1=0, 1 or 2 copies), silent (2+0) carriers were estimated to occur at a frequency of 2 pr, (where p is the frequency of 1 copy of the wild-type (WT) allele and r is the frequency of 0 copy or deletion alleles) which was 1 in 531 AJ individuals. Based on this calculation, the overall carrier frequency for SMA among AJ individuals was approximately 1 in 41.1 (2.4%), which includes carriers identified by MLPA with loss of one SMN1 (1+0) copy, silent (2+0) carriers not detected by dosage-sensitive, location-insensitive methods, and the small fraction of individuals that carry intragenic mutations (0.00047). These values assume that $r^2$ is 0.00014 (Pearns, J Med Genet 15:409-413 (1978)) and that 2% of affected individuals have an intragenic mutation, as has been previously reported (Wirth et al., 1999). The carrier detection rate in the AJ population by MLPA assays was about 90% based on this analysis with about 8% silent (2+0) carriers and about 2% intragenic mutation carriers. Therefore, the residual risk of being a carrier after a negative screening result was 1/402 (Table 2).

Example 3

Mutation Groups Among AJ with Deletions (1+0) or Duplications (2+1)

A total of 23 AJ deletion (1+0) carriers were identified for these studies, including 15 from the above-described population screening and eight that were subsequently identified by MLPA. Four major mutation groups were encountered: 1del) SMN1 deletion only; 2del) SMN1 and SMN2 deletions; 3del) SMN1 exon 7 and 8 deletion and SMN2 deletion, or an SMN1 deletion and SMN2 exon 7 and 8 deletion, and 4del) SMN1 exon 7 and 8 deletion only (Table 5). Interestingly, 32% of AJ individuals with two copies of SMN1 carried a deletion of SMN2 indicating that loss of SMN2 is a common polymorphism in the AJ population and that there may be significant overlap between groups 1del and 2del.

For the gain-of-copy-number duplication group, a total of 72 AJ duplication (2+1) individuals were analyzed by MLPA, including three with four SMN1 copies (2+2), and three major groups were identified: 1dup) three SMN1 copies with no SMN2 copy; 2dup) three SMN1 copies with one SMN2 copy, and 3dup) three SMN1 copies with two SMN2 copies (Table 6). Of the 72 duplication (2+1) individuals examined, 26 (36.1%) had no SMN2 copies, and an additional 32 (44.4%) had one SMN2 copy, indicating that the duplication in these 58 individuals arose by a gene conversion event replacing SMN2 sequences with SMN1 sequences. As noted herein, there may be significant overlap between groups 1dup and 2dup due to the high incidence of SMN2 deletions. Of the SMN1 duplication (2+1) individuals, 11 (15.3%) had two SMN2 copies and, without wishing to be bound by theory, it is expected that those duplications arose by a different mechanism, such as non-allelic homologous recombination (NAHR) or a gene conversion event in individuals with an SMN2 duplication. SMN2 duplications are not uncommon, and were observed by MLPA in the AJ population at a frequency of 1 in 38 (2.6%).

Example 4

Haplotype Reconstruction in AJ with Deletions (1+0) or Duplications (2+1)

Figure 2:
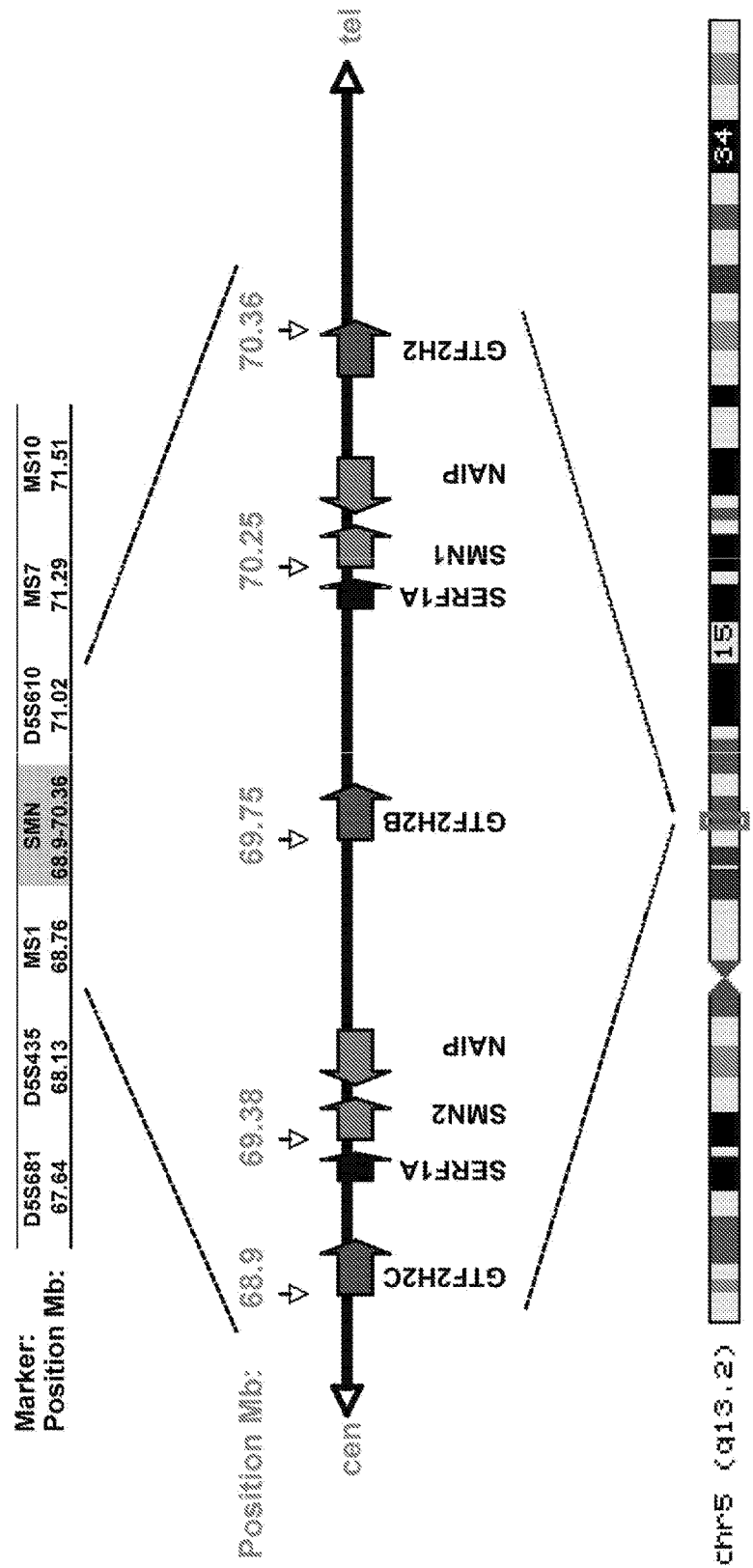
FIG. 2. A schematic of SMA Locus and Flanking Microsatellite Markers at 5q13.2 are shown. At the top of the figure are microsatellite markers used for the analysis of AJ individuals with deletions or duplications of SMN1 (genomic coordinates obtained from the UCSC Genome Browser, NCBI36/HG18). The SMA locus, including the low copy repeats with SMN2 in the proximal copy and SMN1 in the distal copy, are shown below from genomic coordinates 68.9 Mb to 70.36 Mb on 5q13.2. The orientation of each of the genes is indicated by the direction of the arrows and was taken from genomic contig NT_006713.14.

To determine whether founder haplotypes were present for SMN1 deletion (1+0) alleles, 20 carriers from groups 1del, 2del and 3del (see Example 3) that were identified by MLPA were genotyped with six microsatellite markers that span 3.9 Mb on 5q13.2 surrounding the SMN1 locus. They included D5S681 (Genbank NT_006713.15; SEQ ID NO:5), D5S435 (Genbank NT_006713.15; SEQ ID NO:6) and D5S610 (NT_006713.15; SEQ ID NO:7) that flank the SMN1 and SMN2 genes (Scheffer et al., 2001), and three novel markers, MS1 (Genbank NT006713.15; SEQ ID NO:2), MS2 (Genbank NT006713.15; SEQ ID NO:3) and MS3 (Genbank NT006713.15; SEQ ID NO:4) that were created from the publicly available human genomic reference sequence using the UCSC genome database browser. A schematic representation of this region of the human genome is present in FIG. 2. Using these markers, 78 AJ control individuals with two (1+1) SMN1 copies were genotyped. Based on these results, the four consecutive loci chosen for marker association studies were D5S681-D5S435-MS1-D5S610. Their most likely marker configurations are shown in Table 3. Haplotypes for these markers were constructed for the 20 SMN1 deletion (1+0) carriers, including all individuals from groups 1del, 2del, and 3del (Table 5). Group 4del was excluded because all three individuals only had loss of exon 7 and 8 sequences.

Two putative founder haplotypes were significantly enriched (p≤0.001) in the deletion (1+0) carriers as compared to controls. The most common allele combination among the 20 (1+0) carriers examined, 2-5-4-5, was assigned in 22.5% of carriers and was possible in eight additional (40%) carriers. The 2-5-4-5 haplotype also was assigned on only one chromosome of 78 controls (0.6%) indicating that this haplotype was not specific to deletion alleles. The other carrier-specific allele haplotype, 2-1-4-5, was not assigned in any control individuals; however, two control individuals could potentially carry it. One of the group 4del carriers with the SMN1 exon 7 and 8 deletion only could possibly have the 2-5-4-5 haplotype indicating that it may not be specific to SMN1 whole gene copy loss alleles or that it may be the haplotype of the wild-type allele in carrier no. 23 (Table 5).

To analyze the duplication (2+1) individuals for unique shared haplotypes, the six microsatellite markers were genotyped in 69 of the 99 AJ individuals identified with three copies of SMN1 and in three additional AJ individuals that were subsequently identified with four copies of SMN1 (Table 6). The same four marker genotypes, D5S681-D5S435-MS1-D5S610, were used in haplotype reconstruction for 42 duplication (2+1) individuals from groups 1dup and 2dup. Of these, 26 individuals had three SMN1 copies and no SMN2 copies, and 16 had three SMN1 copies and one SMN2 copy; 31 of these duplication (2+1) individuals chosen for the analysis had MS1 allele 6 (Table 8). A separate analysis was performed for the nine group 3dup individuals that carried three SMN1 copies and two SMN2 copies, as they presumably represented a separate duplication group.

The most likely marker haplotypes for the three groups are shown in Table 3. One major duplication marker haplotype, 2-5-6-10, was significantly enriched in Groups 1dup and 2dup (19%). This haplotype was completely absent from the control population and was highly specific for the duplication carriers (p<0.0001). Of the 58 group 1dup and 2dup individuals, 23 (39.7%) had the full four-marker haplotype and eight (13.8%) had the 2-5-6 partial haplotype. In addition, one of the group 3dup individuals (no. 59, Table 6) had the 2-5-6-10 haplotype indicating that this individual most likely carried an SMN2 duplication on the wild-type allele. The major duplication haplotype was also positive in two of the individuals with four SMN1 copies, one of which was homozygous for the 5-6-10 haplotype (no. 70, Table 6). There were two haplotypes that were significantly enriched in group 3dup individuals, 2-5-4-5 and 2-5-9-4, as compared to controls (p<0.0001). The 2-5-4-5 haplotype was also the major deletion haplotype, which was also present in a small fraction of the controls.

Example 5

Sequencing of the Major AJ Duplication Allele

Figure 3A:
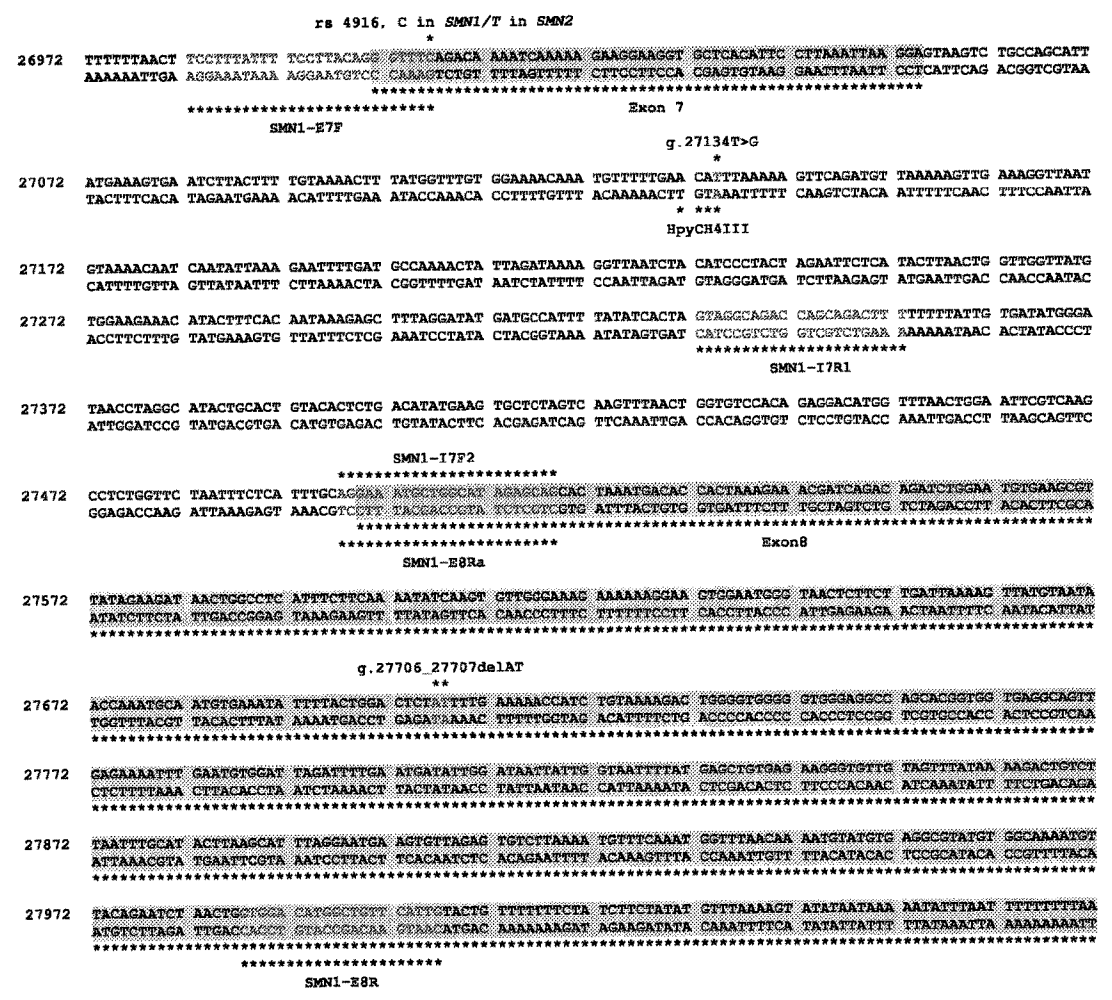

Several putative AJ founder haplotypes were computationally inferred in the SMN1 deletion and duplication alleles. Only the major duplication haplotype, 2-5-6-10, or partial haplotype, 2-5-6, was present in the majority (51.7%) of AJ duplication (2+1) individuals with 0 or 1 copy of SMN2 genotyped (Table 6) and was absent from the AJ control population. The major duplication allele was further scrutinized by sequencing. An SMN1-specific 1025 bp fragment between exons 7 and 8 was amplified from five different AJ individuals with the major duplication allele using primer SMN1-E7F, which includes c.840C at the 3' end, and primer SMN1-E8R (FIG. 3A).

Figure 3B:
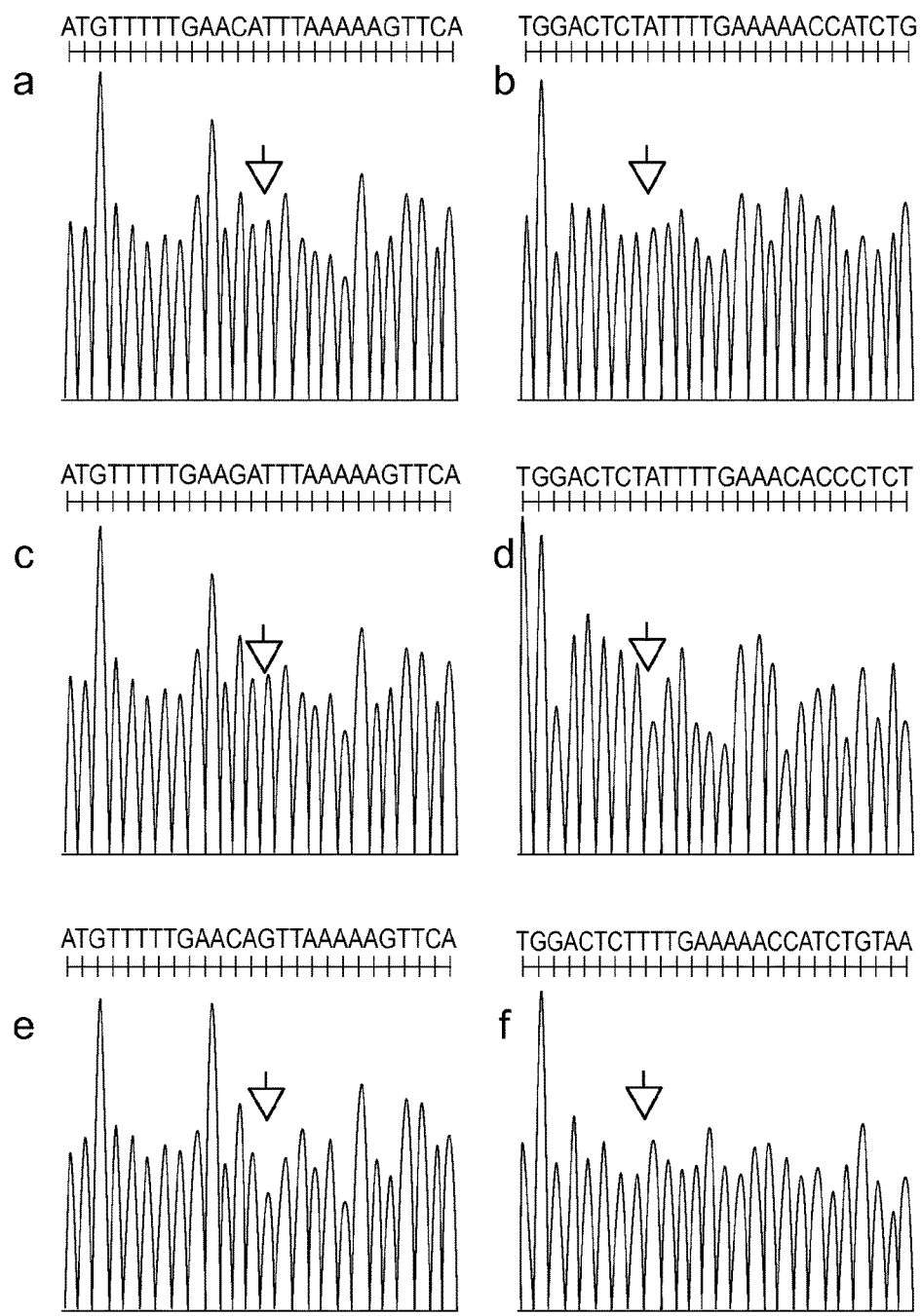
FIG. 3. The g.27134T>G and g.27706_27707 delAT polymorphisms in SMN1 (Genbank Acc. No. NG_008691.1). (A) Partial genomic sequence of SMN1. Exons are shaded. Primer sequences used for amplification and sequencing are denoted by *. Polymorphisms are denoted by dbSNP designation or by genomic coordinates and are indicated above the sequence and denoted by asterisks above (forward primers) or below (reverse primers). (B) Sequence traces that correspond to (a) g.27134T homozygote, (c) g.27134T/G heterozygote, (e) g.27134G homozygote, and g.27706_27707delAT (b) wild-type, (d) g.27706_27707delAT heterozygote, and (f) g.27706_27707delAT homozygote. (C) Gain of an hpyCH4III restriction site created in g.27134T>G. Lanes 10, 11 and 12 depict results with g.27134T (371 bp), lanes 2-7 depict results with individuals heterozygous for g.27134T/G (371 bp, 218 bp and 153 bp) and lanes 1 and 9 show results for individuals homozygous for g.27134G (218 bp and 153 bp). M is the marker lane with a 50 bp ladder shown.
Figure 3:
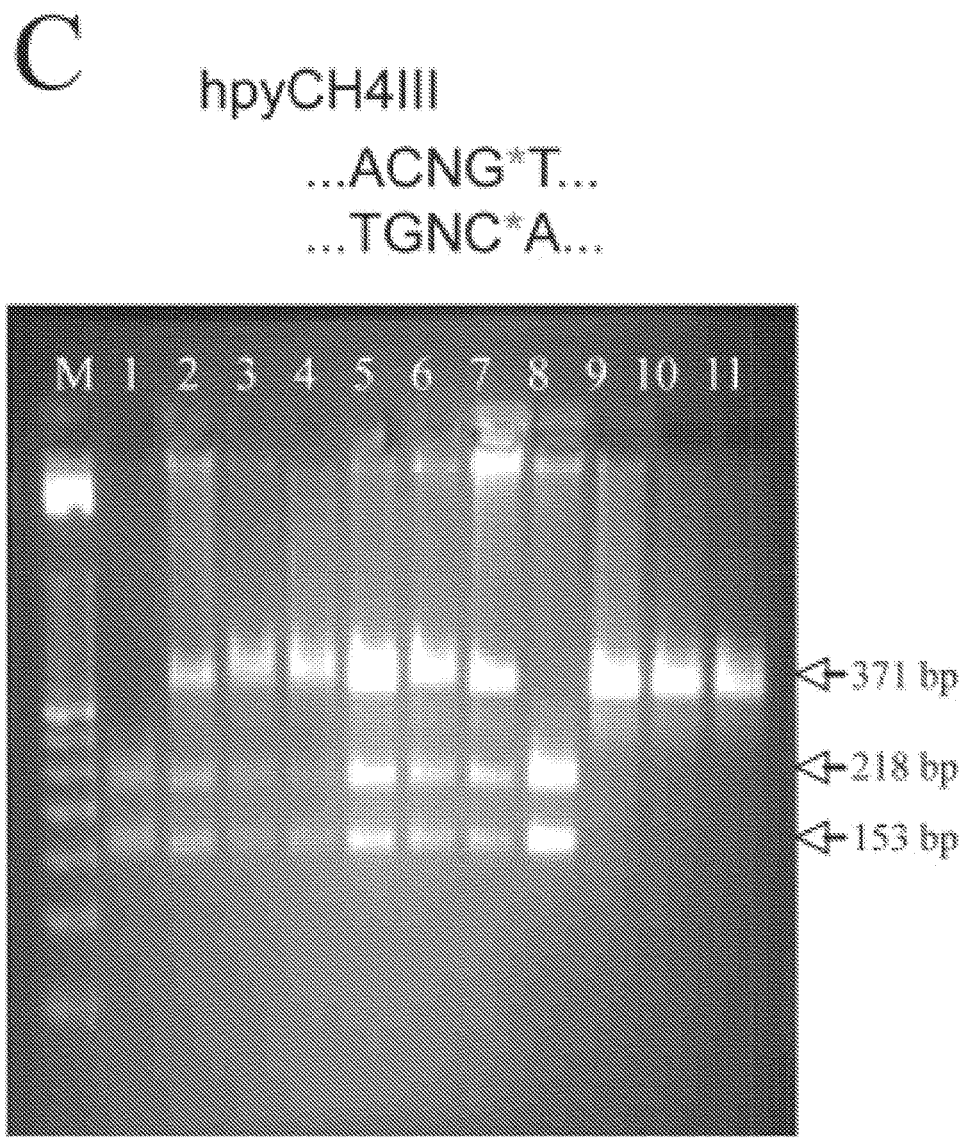

Two sequence variants in the SMN1 gene were identified, g.27134T>G in intron 7 and g.27706_27707 delAT in exon 8 (see Genbank Acc. No. NG_008691.1; FIG. 3B). Neither of these polymorphisms has been previously reported in the NCBI ENTREZ (SNP) database. Further sequence analysis indicated that both polymorphisms were present in all individuals that carried the major duplication haplotype (2-5-6-10) or partial haplotype (2-5-6), and were absent from all other duplication individuals. Thus, each of these polymorphic sequences alone is diagnostic of duplication, as is the combination of both polymorphism sequences. Using a combination of LongRange PCR and TA-cloning analysis, the presence of the two polymorphisms within the same clone in the 12 tested duplication (2+1) individuals indicated that these polymorphisms resided in the same SMN1 allele. No other sequence variants specific to the major duplication allele were identified within the 1025 bp that were analyzed.

Sequencing 1025 bp between SMN1 intron 7 and exon 8 in individuals that carried the major duplication haplotype identified two tightly linked polymorphisms, i.e., g.27134T>G in intron 7 and g.27706_27707 delAT in exon 8. Neither of these polymorphisms had been described in the literature or in the NCBI ENTREZ (SNP) database as being found in or associated with either the SMN1 or SMN2 genes. The g.27134T>G transversion introduced an hpyCH4III restriction site that was present in most of the duplication (2+1) individuals, but not in any of the 315 healthy (1+1) AJ controls tested. Thus, an AJ individual with two copies of SMN1 as determined by MLPA (or another dosage-sensitive method) who is positive for the g.27134T>G generated hpyCH4III cleavage site and its linked g.27706_27707 delAT polymorphism, is highly likely to be an SMN1 silent (2+0) carrier. Therefore, detection of g.27134T>G and/or g.27706_27707 delAT would increase SMA carrier detection in the AJ population from 90% to 94% and reduce the residual risk after a negative carrier screening result from 1 in about 400 to 1 in about 700 (Table 2). Since 83.5% (Table 1) of AJ individuals will have a negative carrier screening result (having two copies of SMN1), this assay can be routinely performed to detect the silent (2+0) carriers among them, thereby increasing SMA carrier detectability. One of skill will recognize, moreover, that convenient RFLP analyses to detect SMA carriers can be conducted with any restriction endonuclease having a site dependent upon the presence or absence of a marker allele spanning that site. Thus, HpyCH4III will distinguish wild type alleles from alleles harboring the g.27134T>G transversion, as will any other restriction endonuclease requiring either the "T" or the "G" at position 27134. All such embodiments of RFLP-based screening or diagnostic-based assays are contemplated in the present disclosure.

Interestingly, the two linked polymorphisms were also present at different frequencies among AA, AS and HI, but not in the EU population. In the AA, AS, and HI populations, the g.27134T>G and g.27706_27707 delAT polymorphisms were more frequent in duplication (2+1) individuals than in those with 1 or 2 SMN1 copies. For example, in the AS population, the linked polymorphisms were exclusive to individuals with SMN1 duplications although they were only present in about 11.5% (3 of 26) of the duplication alleles examined. Testing for these polymorphisms would increase SMA carrier detection by approximately 0.7% in the AS population and would increase carrier detectability to about 93.3% (Table 2). For the AA and HI populations, the linked polymorphisms were not specific to the duplication alleles and were present in a minority of SMN1 single-copy alleles. The AA population has the lowest rate of SMA carrier detection (71%) due to the high prevalence of duplication alleles. Both g.27134T>G and g.27706_27707 delAT were present in the majority of AA duplication alleles (83.7%) indicating that they likely arose from an ancient allele that was involved in the original gene conversion/recombination event that led to the SMN1 duplication, which is present in the AJ, AA, AS and HI populations. None of the (2+1) duplication individuals examined in the AA, HI or AS populations who had the g.27134T>G and g.27706_27707 delAT polymorphisms had the marker MS1 allele 6, which was present in all AJ individuals with the major duplication haplotype. Examination of the extended SMN1 SNP haplotype in individuals that carry g.27134T>G and g.27706_27707 delAT is expected to permit estimation of the date of origin of the duplication allele and confirm whether it is of similar origin in other populations. Expansion of these studies to additional ethnic or demographic groups will be useful in finding specific haplotypes that demarcate the SMN1 deletions or duplications and facilitate identification of silent (2+0) carriers that currently escape detection.

Example 6

RFLP Analysis for the g.27134T>G (Intron7) Polymorphism

Digestion of the PCR amplicons containing g.27134T>G polymorphism with hpyCH4III revealed a restriction site (FIG. 3C) gain attributable to the polymorphism. RFLP analysis of 315 AJ control individuals with two SMN1 copies revealed that none had the hpyCH4III restriction site, indicating that the polymorphism was specific to the major AJ duplication allele. Interestingly, individual no. 69 (Table 6), who was homozygous for the 2-5-6-10 allele combination (Table 6) with four SMN1 copies and no SMN2 copies, was heterozygous for the restriction site, yielding both undigested (391 bp) and digested (153 bp and 218 bp) fragments upon exposure to hypCH4III, consistent with the polymorphism being present in only one copy of the SMN1 duplication. This finding also confirmed the heterozygosity observed for the g.27134T>G and g.27706_27707 delAT polymorphisms among all AJ duplication (2+1) individuals that were sequenced. A total of 49 of the 99 duplication (2+1) individuals identified during the population screening carried the 27134T>G polymorphism as determined by RFLP analysis. Therefore, testing for this polymorphism in the AJ population would increase SMA carrier detection by approximately 4%, identifying about half of the silent (2+0) carriers, for a total detection rate of 94%. Moreover, the residual risk of being an SMA carrier after a negative screening result would decrease from 1 in about 400 to 1 in about 700.

To determine whether the g.27134T>G polymorphism was also present on SMN1 duplication alleles in other ethnic groups, MLPA and RFLP analyses were performed on genomic DNAs from 276 African American (AA), 250 Asian (AS), 262 Hispanic (HI) and 137 European (EU) individuals. The results, summarized in Table 4, indicate that g.27134T>G was present on duplication alleles in all populations examined except for the EU individuals. In the AA population, the RFLP was observed in individuals with 1, 2, 3 or 4 copies of SMN1 indicating that it is not specific to their duplication alleles. The majority (81%) of AA duplication (2+1) individuals, however, were heterozygous for g.27134T>G, while only 21% of individuals with two copies (1+1) of SMN1 were positive for the polymorphism. Of note, one of the five AA deletion carriers was positive for the RFLP, presumably on the wild-type allele. Similarly, the RFLP was present in about half of HI duplication (2+1) individuals, but it also was present in approximately 5.5% of wild-type alleles. Conversely, in the AS population, the RFLP was not found in wild-type alleles, but was present only in about 14% of the duplication (2+1) individuals. Sequencing was performed on 142 AA, 2 AS and 5 HI individuals that were positive for the RFLP to confirm that both g.27134T>G and g.27706_27707 delAT variants were present on the RFLP-positive alleles. In all cases examined, the two polymorphisms occurred together within the same SMN1 allele, regardless of how many copies of SMN1 were present.

Example 7

Improved Identification of SMA Carriers in Various Racial and Ethnic Groups

The promising results disclosed in the preceding examples established that the method of detecting chromosomally unbalanced SMN1 loads, such as is found in silent (2+0) SMA carriers, can appreciably improve the identification of SMA carriers in ethnic and racial groups, and in particular, in the Ashkenazi Jewish (AJ) population. The data further showed that SMA carrier identification was improved in Asians, and gave some indication that the method had an even broader range of improving the detection of chromosomally unbalanced SMN1 loads across various ethnic and racial groups. The data provided in Table 9 reveals the residual risks of being a carrier after screening positive and negative for g.27134T>G in intron 7 and g.27706_27707 delAT in exon 8. Apparent from Table 9 is that the identification method disclosed herein improves the detection of chromosomally unbalanced SMN1 loads, leading to increased detection of SMA carriers, such as silent (2+0) SMA carriers, in a variety of ethnic and racial groups, including AJ, Asians, African Americans and Hispanics.

The implications of these results for genetic counseling and family planning are significant. With the method disclosed herein, a more accurate assessment can be made of the modified risk of having a child with SMA if one partner is a known carrier and the other has two copies of SMN1, as disclosed in Table 10. The data show that adding the dosage-sensitive, location-sensitive method of identifying SMA carriers leads to a significant reduction in potentially devastating false negative outcomes, in which potential parents mistakenly believe they can reproduce without significant risk of SMA offspring. The data in Table 10 establish that the benefit of reducing the frequency of false negative outcomes attributable to the method disclosed herein spans ethnic and racial groups and is, therefore, of widespread value to human populations.

Beyond the polymorphisms disclosed in the examples above, additional polymorphisms are expected to be useful in assessing the residual risk of SMA due to the carrier status of one or both parents. As catalogued in Table 11, these novel polymorphisms can occur throughout the SMN1 gene, including within introns 1, 2a, 6, 7 and 8. With these polymorphisms and the polymorphisms disclosed above, the risk of erring in identifying SMA carrier status is minimized, allowing potential parents, guided by genetic counselors, to be better informed in making family planning decisions.

TABLE 1

SMN1 Carrier Screening of 692 Ashkenazi Jewish Individuals

| SMN1 copy number | Genotype | n | % | Expected* (n) | Expected* (%) |
|---|---|---|---|---|---|
| 0 | 0 + 0 | 0 | 0 | 0.1 | 0.01 |
| 1 | 1 + 0 | 15 | 2 | 14 | 2 |
| 2 | 1 + 1 | 578 | 84 | 583 | 84 |
|   | 2 + 0 | — | — | 1 | 0.2 |
| 3 | 1 + 2 | 99 | 14 | 91 | 13 |
| 4 | 2 + 2 | 0 | 0.0 | 4 | 0.5 |

*Expected frequencies were calculated using the observed wild-type ($p^2$ with 2 SMN1 copies) and the observed carrier frequency (2pq with 1 SMN1 copy) and the equation $p^2 + 2pq + q^2 + 2qr + 2pr + r^2 = 1$

TABLE 2

SMA Carrier Detection and Residual Risk with addition of SMN1 g.27134T > G and g.27706_27707delAT

| Ethnicity | Carrier Frequency | Detection Rate | Residual risk after negative carrier screen | Detection rate with addition of SMN1 g.27134T > G and g.27706_27707delAT | Residual risk after negative result for SMN1 g.27134T > G and g.27706_27707delAT |
|---|---|---|---|---|---|
| Ashkenazi Jewish | 1 in 41.1 | 90% | 1 in 402 | 94% | 1 in 683 |
| Asian | 1 in 53* | 92.6%* | 1 in 628* | 93.3% | 1 in 765 |

*Taken from Hendrickson BC, Donohoe C, Akmaev VR, Sugarman EA, Labrousse P, Boguslavskiy L, Flynn K, Rohlfs EM, Walker A, Allitto B, Sears C, Scholl T Differences in SMN1 allele frequencies among ethnic groups within North America. *J. Med. Genet.* 2009; 46: 641-44.

TABLE 3

Haplotype Analysis for SMA Locus.

| Marker | D5S681 | D5S435 | MS1 | D5S610 | Haplotype frequency in WT, % (N = 78) | Haplotype frequency in Carriers, % | P-value |
|---|---|---|---|---|---|---|---|
| SMN1 | 2 | 1 | 4 | 4 | 0 | 7.5 | 1.0 |
| Deletion | 2 | 1 | 4 | 5 | 0 | 10.0 | 0.001 |
| Carriers | 2 | 5 | 4 | 5 | 0.6 | 22.5 | <.0001 |
| (N = 20) | 2 | 5 | 7 | 5 | 1.4 | 5.0 | 0.19 |
|  |  |  | Overall P-value <.0001 |  |  |  |  |
| SMN1 | 2 | 3 | 7 | 5 | 0 | 4.7 | 0.01 |
| Duplication | 2 | 5 | 3 | 4 | 2.6 | 3.6 | 0.12 |
| Groups 1dup | 2 | 5 | 6 | 10 | 0 | 19.0 | <.0001 |

TABLE 3-continued

Haplotype Analysis for SMA Locus.

| Marker | D5S681 | D5S435 | MS1 | D5S610 | Haplotype frequency in WT, % (N = 78) | Haplotype frequency in Carriers, % | P-value |
|---|---|---|---|---|---|---|---|
| & 2dup | 2 | 5 | 9 | 2 | 1.8 | 4.8 | 0.19 |
| (N = 42) | 4 | 3 | 4 | 2 | 0 | 3.4 | 0.03 |
|  | 4 | 5 | 4 | 2 | 0.8 | 3.6 | 0.003 |
|  | Overall P-value <.0001 | | | | | | |
| SMN1 | 2 | 4 | 9 | 5 | 0 | 5.6 | 0.035 |
| Duplication | 2 | 5 | 4 | 5 | 0.6 | 11.1 | <.0001 |
| Group 3dup | 2 | 5 | 7 | 2 | 0 | 5.6 | 1.0 |
| (N = 9) | 2 | 5 | 9 | 4 | 0 | 16.7 | <.0001 |
|  | 4 | 1 | 4 | 10 | 0 | 5.6 | 1.0 |
|  | 4 | 5 | 4 | 9 | 1.8 | 11.1 | 0.02 |
|  | 6 | 4 | 4 | 5 | 0 | 5.6 | 0.025 |
|  | 7 | 3 | 2 | 5 | 0 | 5.6 | 0.003 |
|  | Overall P-value <.0001 | | | | | | |

Haplotypes shown in boldface represent significance with comparison to wild-type (WT) (2 copies) frequencies. Only haplotypes with a frequency above 3% in carriers are shown.

TABLE 4

SMN1 Population Screening Data for g.27134T > G RFLP

| Ethnicity | SMN1 copy number | RFLP Negative | RFLP Heterozygous | RFLP Homozygous | Total |
|---|---|---|---|---|---|
| Ashkenazi Jewish | 2 | 315 | 0 | 0 | 315 |
| African American | 1 | 4 | 0 | 1 | 5 |
|  | 2 | 108 | 26 | 2 | 136 |
|  | 3 | 21 | 86 | 4 | 111 |
|  | 4 | 1 | 23 | 0 | 24 |
| Asian | 1 | 2 | 0 | 0 | 2 |
|  | 2 | 222 | 0 | 0 | 222 |
|  | 3 | 20 | 2 | 0 | 22 |
|  | 4 | 1 | 1 | 0 | 2 |
| Hispanic | 1 | 1 | 0 | 0 | 1 |
|  | 2 | 206 | 12 | 1 | 219 |
|  | 3 | 20 | 20 | 0 | 40 |
|  | 4 | 0 | 2 | 0 | 2 |
| European | 1 | 12 | 0 | 0 | 12 |
|  | 2 | 413 | 2 | 0 | 415 |
|  | 3 | 23 | 4 | 0 | 27 |
|  | 4 | 2 | 2 | 0 | 4 |

TABLE 5

Microsatellite Analysis of AJ Deletion Carriers

| MARKER | | D5S681 | D5S435 | MS1 | SMN | D5S610 | MS2 | MS3 |
|---|---|---|---|---|---|---|---|---|
| PHYSICAL LOC (Mb) | | 67.64 | 68.13 | 68.76 | 68.9-70.36 | 71.02 | 71.29 | 71.51 |
| MLPA copy number | Sample # | | | | | | | |
| Group 1del | 1 | 2.4 | 2.5 | 4.5 | | 2.5 | 1.4 | 1.2 |
| SMN1/SMN2 | 2 | 2.2 | 1.6 | 3.4 | | 2.5 | 2.4 | 2.2 |
| (1/1) | 3 | 2.2 | 1.5 | 4.10 | | 2.4 | 4.10 | 1.2 |
|  | 4 | 2.4 | 1.3 | 4.4 | | 2.5 | 4.6 | 2.4 |
|  | 5 | 2.4 | 4.5 | 1.4 | | 5.5 | 5.5 | 3.4 |
| Group 2del | 6 | 2.4 | 1.1 | 4.8 | | 5.11 | 4.5 | 2.2 |
| SMN1/SMN2 | 7 | 2.5 | 1.5 | 3.8 | | 2.3 | 5.5 | 1.2 |
| (1/2) | 8 | 1.2 | 1.5 | 3.7 | | 4.5 | 4.5 | 1.3 |
|  | 9 | 2.2 | 1.5 | 4.5 | | 1.5 | 4.5 | 2.2 |
|  | 10 | 2.2 | 5.5 | 4.7 | | 5.5 | 1.4 | 2.3 |
|  | 11 | 2.4 | 1.3 | 4.11 | | 5.5 | 2.4 | 1.2 |
|  | 12 | 2.4 | 1.4 | 4.4 | | 4.9 | 2.10 | 3.6 |
|  | 13 | 2.4 | 1.3 | 4.5 | | 4.9 | 4.6 | 2.2 |
|  | 14 | 2.9 | 1.5 | 4.8 | | 5.7 | 1.4 | 2.4 |
|  | 15 | 1.4 | 3.5 | 5.15 | | 4.4 | 4.5 | 1.2 |
|  | 16 | 2.6 | 4.5 | 1.4 | | 5.12 | 5.5 | 1.3 |
|  | 17 | 2.2 | 1.5 | 4.13 | | 4.5 | 5.5 | 1.3 |
| Group 3del | 18 | 3.6 | 3.5 | 3.4 | | 2.10 | 2.5 | 1.3 |
| SMN1/SMN2 | 19 | 2.6 | 1.5 | 4.4 | | 4.5 | 4.6 | 2.2 |
| (1/del ex7, ex8) or | 20 | 2.2 | 5.5 | 4.7 | | 5.9 | 4.4 | 1.3 |
| (del ex7, ex8/1) | | | | | | | | |
| Group 4del | 21 | 2.4 | 3.5 | 4.9 | | 2.9 | 4.5 | 2.2 |
| SMN1/SMN2 | 22 | 3.5 | 4.5 | 2.4 | | 4.5 | 3.6 | 1.2 |
| (del ex7, ex8/2) | 23 | 2.4 | 1.5 | 4.4 | | 5.6 | 4.5 | 2.3 |

TABLE 6

Microsatellite Analysis of AJ Duplication Carriers

| MLPA copy number | MARKER<br>PHYSICAL LOC (Mb)<br>Sample # | D5S681<br>67.64 | D5S435<br>68.13 | MS1<br>68.76 | SMN<br>68.9-70.36 | D5S610<br>71.02 | MS2<br>71.29 | MS3<br>71.51 |
|---|---|---|---|---|---|---|---|---|
| Group 1dup<br>SMN1/SMN2<br>(3/0) | 1 | 2.4 | 4.5 | 6.8 | | 6.10 | 2.4 | 1.1 |
| | 2 | 2.3 | 3.5 | 4.6 | | 2.10 | 2.5 | 1.1 |
| | 3 | 2.3 | 5.5 | 6.9 | | 2.10 | 2.4 | 1.4 |
| | 4 | 2.4 | 5.5 | 6.9 | | 4.10 | 2.2 | 2.2 |
| | 5 | 2.2 | 3.5 | 4.6 | | 5.10 | 4.5 | 1.2 |
| | 6 | 2.4 | 5.6 | 4.6 | | 5.10 | 4.4 | 1.2 |
| | 7 | 2.4 | 4.5 | 6.9 | | 9.10 | 4.4 | 1.1 |
| | 8 | 2.4 | 4.5 | 6.9 | | 5.10 | 2.4 | 2.3 |
| | 9 | 2.2 | 3.5 | 2.6 | | 5.10 | 2 | 1.2 |
| | 10 | 2.2 | 5.5 | 4.6 | | 9.10 | 4.4 | 1.6 |
| | 11 | 2.2 | 4.5 | 5.6 | | 4.10 | 2.5 | 1.2 |
| | 12 | 10.11 | 2.5 | 5.6 | | 4.10 | 2.4 | 1.2 |
| | 13 | 2.6 | 5.5 | 3.6 | | 4.9 | 4.10 | 1.3 |
| | 14 | 2.6 | 3.5 | 4.6 | | 2.5 | 2.4 | 1.2 |
| | 15 | 2.3 | 1.5 | 4.6 | | 4.11 | 3.5 | 2.2 |
| | 16 | 2.10 | 2.5 | 6.17 | | 2.2 | 2.4 | 1.2 |
| | 17 | 2.2 | 2.5 | 6.12 | | 2.2 | 2.4 | 1.2 |
| | 18 | 2.4 | 1.5 | 3.5 | | 4.4 | 2.4 | 1.2 |
| | 19 | 2.4 | 5.5 | 3.5 | | 2.6 | 4.5 | 1.1 |
| | 20 | 2.2 | 1.4 | 4.4 | | 6.9 | 4.5 | 1.1 |
| | 21 | 4.6 | 5.5 | 4.5 | | 6.9 | 5.5 | 1.2 |
| | 22 | 2.6 | 1.4 | 4.9 | | 2.10 | 5.6 | 1.2 |
| | 23 | 2.4 | 3.3 | 4.7 | | 2.5 | 2.6 | 4.6 |
| | 24 | 2.4 | 3.3 | 7.7 | | 5.5 | 2.2 | 2.6 |
| | 25 | 2.6 | 3.5 | 4.7 | | 5.5 | 2.6 | 2.6 |
| | 26 | 2.4 | 4.5 | 4.4 | | 6.7 | 3.4 | 1.2 |
| Group 2dup<br>SMN1/SMN2<br>(3/1) | 27 | 2.7 | 3.5 | 5.6 | | 8.10 | 10.5 | 2.3 |
| | 28 | 2.2 | 1.5 | 8.6 | | 10.11 | 4.5 | 2.4 |
| | 29 | 2.4 | 5.5 | 4.6 | | 2.10 | 4.5 | 1.2 |
| | 30 | 4.4 | 3.5 | 4.6 | | 2.10 | 2.4 | 2.5 |
| | 31 | 2.4 | 5.5 | 5.6 | | 2.10 | 2 | 1.2 |
| | 32 | 2.3 | 1.5 | 8.6 | | 9.10 | 4 | 2.4 |
| | 33 | 2.8 | 4.5 | 4.6 | | 5.10 | 2.6 | 1.2 |
| | 34 | 2.2 | 4.5 | 4.6 | | 4.10 | 2.10 | 2.2 |
| | 35 | 2.2 | 3.5 | 4.6 | | 2.10 | 2.4 | 2.2 |
| | 36 | 2.4 | 5.5 | 6.8 | | 6.10 | 2.5 | 1.5 |
| | 37 | 2.4 | 1.5 | 4.6 | | 2.5 | 4.4 | 1.3 |
| | 38 | 2.4 | 3.5 | 4.6 | | 2.9 | 4.4 | 2.4 |
| | 39 | 2.2 | 5.5 | 13.6 | | 5.9 | 2.5 | 1.3 |
| | 40 | 2.2 | 4.5 | 4.6 | | 5.9 | 6.10 | 3.4 |
| | 41 | 2.4 | 5.5 | 5.9 | | 2.6 | 5.7 | 1.2 |
| | 42 | 2.4 | 2.5 | 5.9 | | 2.6 | 5.7 | 1.2 |
| | 43 | 2.6 | 5.5 | 3.4 | | 4.9 | 4.4 | 3.4 |
| | 44 | 2.7 | 5.5 | 3.4 | | 4.11 | 4.4 | 2.4 |
| | 45 | 2.5 | 1.5 | 3.5 | | 4.4 | 4.6 | 1.2 |
| | 46 | 2.4 | 3.5 | 3.5 | | 2.4 | 2.4 | 2.4 |
| | 47 | 2.2 | 5.5 | 4.5 | | 9.11 | 8.5 | 1.2 |
| | 48 | 2.2 | 4.4 | 4.4 | | 4.5 | 2.8 | 1.5 |
| | 49 | 4.6 | 5.7 | 1.4 | | 2.5 | 2.4 | 1.3 |
| | 50 | 2.6 | 5.5 | 7.9 | | 2.5 | 2.6 | 6.1 |
| | 51 | 2.2 | 1.5 | 7.9 | | 2.5 | 2.2 | 6.4 |
| | 52 | 2.4 | 3.8 | 5.7 | | 5.9 | 2.5 | 6.6 |
| | 53 | 2.2 | 1.3 | 3.7 | | 2.5 | 2.5 | 1.2 |
| | 54 | 2.2 | 3.5 | 4.7 | | 5.5 | 2.4 | 6.3 |
| | 55 | 3.4 | 5.8 | 5.7 | | 5.9 | 2.5 | 6.6 |
| | 56 | 2.4 | 3.10 | 7.9 | | 1.2 | 2.5 | 1.2 |
| | 57 | 2.4 | 3.4 | 2.10 | | 5.5 | 2.4 | 1.3 |
| | 58 | 2.5 | 3.5 | 5.9 | | 2.8 | 4.10 | 1.2 |
| Group 3dup<br>SMN1/SMN2<br>(3/2) | 59 | 2.4 | 3.5 | 3.6 | | 4.10 | 2.5 | 2.4 |
| | 60 | 2.7 | 3.5 | 2.9 | | 4.5 | 2.4 | 2.9 |
| | 61 | 2.2 | 4.5 | 9 | | 4.5 | 4 | 3.9 |
| | 62 | 2.4 | 5.5 | 4.9 | | 4.9 | 4.5 | 1.3 |
| | 63 | 2.2 | 5.5 | 4.7 | | 2.5 | 2.4 | 1.3 |
| | 64 | 4.6 | 3.3 | 2.8 | | 5.9 | 2.5 | 1.2 |
| | 65 | 2.6 | 1.1 | 3.3 | | 5.11 | 2.4 | 1.2 |
| | 66 | 2.4 | 1.5 | 4.4 | | 5.10 | 2.5 | 3.5 |
| | 67 | 4.6 | 4.5 | 4.4 | | 5.9 | 9.10 | 1.3 |
| | 68 | 2.6 | 3.5 | 2.10 | | 2.5 | NA | NA |
| | 69 | 2.10 | 3.4 | 3.5 | | 5.5 | 4.9 | 1.3 |
| SMN1/SMN2<br>(4/0) | 70 | 2.5 | 5.5 | 6.6 | | 10.10 | 2.4 | 2.4 |
| | 71 | 3.7 | 7.7 | 4.9 | | 9.12 | 3.5 | 2.2 |
| | 72 | 2.5 | 2.5 | 6.9 | | 2.10 | 4.4 | 1.1 |

NA = Not Analyzed

TABLE 7

Microsatellite Analysis of AJ Controls - 2 copies of SMN1

| MARKER PHYSICAL LOC (Mb) Sample # | D5S681 67.64 | D5S435 68.13 | MS1 68.76 | SMN 68.9-70.36 | D5S610 71.02 | MS2 71.29 | MS3 71.51 |
|---|---|---|---|---|---|---|---|
| 1 | 2.4 | 4.5 | 4.5 | | 2.5 | 2.4 | 2.3 |
| 2 | 1.2 | 5.5 | 3.4 | | 4.5 | 4.4 | 2.2 |
| 3 | 2.4 | 5.5 | 4.4 | | 5.5 | 4.4 | 3.3 |
| 4 | 4.5 | 5.7 | 4.6 | | 5.7 | 4.5 | 1.2 |
| 5 | 2.4 | 5.5 | 3.4 | | 5.11 | 5.10 | 1.6 |
| 6 | 4.4 | 5.9 | 4.11 | | 2.5 | 2.2 | 2.2 |
| 7 | 2.4 | 1.5 | 3.4 | | 4.5 | 2.7 | 1.3 |
| 8 | 1.2 | 4.4 | 3.4 | | 5.9 | 4.6 | 1.2 |
| 9 | 3.3 | 1.3 | 4.7 | | 4.5 | 2.4 | 1.1 |
| 10 | 1.1 | 7.8 | 4.5 | | 5.11 | 2.4 | 1.3 |
| 11 | 2.5 | 1.4 | 3.5 | | 2.10 | 4.5 | 2.5 |
| 12 | 2.4 | 4.5 | 4.9 | | 2.4 | 2.4 | 3.3 |
| 13 | 2.4 | 5.5 | 3.3 | | 2.5 | 2.5 | 1.2 |
| 14 | 4.4 | 5.5 | 4.7 | | 2.11 | 5.5 | 1.2 |
| 15 | 2.5 | 1.3 | 3.4 | | 1.3 | 5.5 | 2.2 |
| 16 | 2.2 | 1.5 | 1.5 | | 4.5 | 5.6 | 3.3 |
| 17 | 2.4 | 1.1 | 3.6 | | 2.6 | 1.10 | 2.4 |
| 18 | 2.6 | 3.4 | 4.5 | | 7.8 | 5.10 | 3.4 |
| 19 | 2.6 | 4.5 | 4.5 | | 9.10 | 2.4 | 1.1 |
| 20 | 1.2 | 1.1 | 3.8 | | 3.11 | 8.8 | 1.2 |
| 21 | 2.3 | 1.4 | 4.6 | | 5.9 | 4.9 | 1.2 |
| 22 | 3.7 | 4.4 | 4.7 | | 2.7 | 3.6 | 1.2 |
| 23 | 4.5 | 4.5 | 4.4 | | 4.7 | 5.10 | 3.3 |
| 24 | 2.7 | 4.4 | 4.5 | | 9.9 | 5.5 | 1.1 |
| 25 | 2.4 | 1.5 | 4.6 | | 2.11 | 4.5 | 1.2 |
| 26 | 4.6 | 1.4 | 4.9 | | 2.2 | 3.5 | 1.2 |
| 27 | 2.4 | 4.5 | 7.10 | | 2.5 | 4.5 | 2.3 |
| 28 | 2.4 | 4.5 | 9.9 | | 5.9 | 2.5 | 1.2 |
| 29 | 4.4 | 3.10 | 3.5 | | 2.4 | 2.4 | 1.4 |
| 30 | 2.2 | 1.5 | 3.10 | | 11.11 | 4.5 | 1.2 |
| 31 | 2.4 | 1.3 | 5.11 | | 2.11 | 2.4 | 2.5 |
| 32 | 2.3 | 5.5 | 7.10 | | 2.5 | 2.4 | 2.2 |
| 33 | 2.6 | 3.5 | 4.5 | | 2.4 | 4.5 | 2.2 |
| 34 | 5.6 | 5.5 | 4.7 | | 5.5 | 2.6 | 2.4 |
| 35 | 6.10 | 3.4 | 4.9 | | 2.5 | 4.9 | 1.4 |
| 36 | 2.9 | 1.3 | 4.8 | | 2.7 | 4.4 | 2.4 |
| 37 | 2.4 | 3.5 | 4.6 | | 2.5 | 4.10 | 2.2 |
| 38 | 2.4 | 4.5 | 3.5 | | 4.9 | 2.4 | 1.4 |
| 39 | 2.4 | 3.5 | 5.7 | | 2.2 | 4.9 | 1.1 |
| 40 | 3.5 | 5.5 | 4.7 | | 2.5 | 2.2 | 2.4 |
| 41 | 1.4 | 5.5 | 4.7 | | 2.6 | 1.10 | 1.1 |
| 42 | 2.2 | 3.5 | 2.3 | | 2.5 | 2.10 | 1.2 |
| 43 | 4.5 | 3.5 | 2.9 | | 5.5 | 2.2 | 2.2 |
| 44 | 4.4 | 5.5 | 4.4 | | 5.9 | 3.5 | 2.3 |
| 45 | 2.4 | 3.5 | 5.5 | | 2.2 | 2.9 | 2.4 |
| 46 | 4.4 | 4.5 | 4.9 | | 2.11 | 4.5 | 1.2 |
| 47 | 2.2 | 5.5 | 3.4 | | 4.10 | 4.5 | 2.3 |
| 48 | 2.4 | 1.5 | 4.6 | | 2.9 | 1.4 | 1.1 |
| 49 | 4.4 | 3.4 | 4.4 | | 4.9 | 2.10 | 3.3 |
| 50 | 2.2 | 1.3 | 4.5 | | 5.9 | 5.6 | 1.3 |
| 51 | 2.2 | 5.5 | 3.4 | | 5.6 | 2.6 | 1.2 |
| 52 | 2.4 | 1.5 | 3.7 | | 2.4 | 4.5 | 2.2 |
| 53 | 2.4 | 4.5 | 5.9 | | 2.5 | 5.5 | 1.2 |
| 54 | 2.7 | 5.5 | 3.4 | | 10.10 | 3.4 | 1.2 |
| 55 | 1.4 | 2.8 | 4.5 | | 2.4 | 3.4 | 1.3 |
| 56 | 2.2 | 3.5 | 3.5 | | 2.3 | 2.2 | 3.4 |
| 57 | 2.3 | 5.5 | 9.9 | | 2.12 | 2.4 | 1.5 |
| 58 | 2.4 | 4.5 | 5.9 | | 2.9 | 4.6 | 1.1 |
| 59 | 2.2 | 5.5 | 3.3 | | 8.8 | 2.2 | 3.3 |
| 60 | 2.4 | 5.5 | 4.5 | | 2.4 | 2.4 | 1.2 |
| 61 | 2.2 | 5.5 | 3.8 | | 4.9 | 5.5 | 1.3 |
| 62 | 4.5 | 3.5 | 4.14 | | 2.5 | 3.4 | 1.3 |
| 63 | 2.2 | 5.5 | 3.8 | | 5.7 | 5.5 | 1.1 |
| 64 | 4.4 | 3.4 | 4.5 | | 2.6 | 2.4 | 3.4 |
| 65 | 2.4 | 3.5 | 4.4 | | 2.9 | 1.2 | 1.3 |
| 66 | 3.4 | 3.4 | 3.4 | | 2.6 | 2.5 | 3.4 |
| 67 | 3.4 | 5.5 | 7.8 | | 5.6 | 2.5 | 2.3 |
| 68 | 3.6 | 1.5 | 4.4 | | 2.9 | 3.6 | 1.1 |
| 69 | 2.4 | 1.5 | 3.5 | | 4.9 | 4.6 | 1.2 |
| 70 | 2.2 | 3.5 | 3.5 | | 2.2 | 2.9 | 3.4 |
| 71 | 2.4 | 5.5 | 3.7 | | 4.5 | 4.10 | 3.4 |
| 72 | 3.8 | 1.1 | 4.8 | | 9.10 | 2.4 | 2.2 |
| 73 | 2.2 | 3.5 | 5.7 | | 5.11 | 5.10 | 1.2 |
| 74 | 2.4 | 5.5 | 3.3 | | 4.5 | 5.5 | 2.3 |

TABLE 7-continued

Microsatellite Analysis of AJ Controls - 2 copies of SMN1

| MARKER PHYSICAL LOC (Mb) Sample # | D5S681 67.64 | D5S435 68.13 | MS1 68.76 | SMN 68.9-70.36 | D5S610 71.02 | MS2 71.29 | MS3 71.51 |
|---|---|---|---|---|---|---|---|
| 75 | 2.6 | 3.8 | 5.5 | | 2.11 | 2.2 | 3.3 |
| 76 | 4.5 | 5.5 | 4.9 | | 2.11 | 3.5 | 2.6 |
| 77 | 2.6 | 1.5 | 3.4 | | 2.5 | 2.4 | 1.3 |
| 78 | 2.4 | 4.5 | 4.4 | | 4.7 | 5.5 | 2.2 |

TABLE 8

Allele marker lengths

| | PHYSICAL LOC (Mb) | | | |
|---|---|---|---|---|
| Alleles for Marker | 67.64 D5S681 | 68.13 D5S435 | 68.76 MS1 | 71.02 D5S610 |
| 1 | 143 | 122 | 98 | 124 |
| 2 | 145 | 124 | 114 | 128 |
| 3 | 149 | 130 | 116 | 132 |
| 4 | 151 | 132 | 118 | 139 |
| 5 | 155 | 134 | 120 | 141 |
| 6 | 157 | 138 | 122 | 134 |
| 7 | 141 | 126 | 124 | 136 |
| 8 | 147 | 128 | 126 | 143 |
| 9 | 153 | 140 | 128 | 126 |
| 10 | 137 | 136 | 130 | 117 |
| 11 | 128 | 116 | 132 | 130 |
| 12 | | | 136 | 147 |
| 13 | | | 112 | |
| 14 | | | 134 | |
| 15 | | | 102 | |
| 16 | | | 106 | |
| 17 | | | 108 | |

TABLE 9

SMA Carrier Detection and Residual Risk with addition of SMN1 g.27134T>G and g.27706_27707delAT

| Ethnicity | Carrier Frequency | Detection Rate | Residual risk after negative carrier screen with 2copies of SMN1 | Detection rate with addition of SMN1 g. 27134T>G and g.27706_27707delAT with 2copies of SMN1 | Residual risk after negative result for SMN1 g.27134T>G and g.27706_27707delAT with 2copies of SMN1 | Residual risk after positive result for SMN1 g.27134T>G and g.27706_27707delAT with 2copies of SMN1 |
|---|---|---|---|---|---|---|
| Ashkenazi Jewish | 1 in 41.1 | 90% | 1 in 345 | 94% | 1 in 580 | carrier |
| Asian | 1 in 53[1] | 92.6%[1] | 1 in 628[1] | 93.3% | 1 in 701.8 | carrier |
| African American | 1 in 66[1] | 71.1%[1] | 1 in 121[1] | N/A | 1 in 395.7 | 1 in 33.5 |
| Hispanic | 1 in 117[1] | 90.6%[1] | 1 in 1061[1] | N/A | 1 in 1762 | 1 in 139.6 |
| Caucasian | 1 in 35[1] | 94.9%[1] | 1 in 632[1] | N/A | 1 in 769.3 | 1 in 28.6 |

N/A—not applicable or cannot be calculated,
[1]Hendrickson et al., 2009

TABLE 10

Risk of having a child with SMA if one member of a couple is a known carrier and the other has two copies of SMN1

| Ethnicity of partner with 2 copies of SMN1 | Negative result by dosage sensitive methods | Negative result for SMN1 g.27134T > G and g.27706_27707delAT | Positive result for SMN1 g.27134T > G and g.27706_27707delAT |
|---|---|---|---|
| Ashkenazi Jewish | 1 in 1380 | 1 in 2320 | 1 in 4 |
| Asian | 1 in 2512 | 1 in 2807 | 1 in 4 |
| African American | 1 in 484 | 1 in 1583 | 1 in 134 |
| Hispanic | 1 in 4244 | 1 in 7048 | 1 in 558.4 |
| Caucasian | 1 in 2528 | 1 in 3185 | 1 in 114 |

TABLE 11

List of novel sequence variants identified on the AJ and AA RFLP + duplication alleles

| Chr. 5 Position | Ethnicity SMN1 duplication RFLP status SMN1 Gen. Position | Exon/ Intron | Ref. Nuc. | AJ dup/ RFLP_het Seq. | AJ dup/ RFLP_wt Seq. | AJ non dup/ RFLP_wt Seq. | AA dup/ RFLP_homo Seq. | AA dup/ RFLP_het Seq. | AA dup/ RFLP_wt Seq. | Seq. Method |
|---|---|---|---|---|---|---|---|---|---|---|
| 70232445 | 11678 | Intron 1 | G | G<u>T</u> | G | G | <u>T</u> | G<u>T</u> | G | NGS w/Sanger |
| 70236541 | 15774 | Intron2a | G | G<u>A</u> | G | G | <u>A</u> | G<u>A</u> | G | NGS w/Sanger |
| 70243571 | 22804 | Intron 6 | G | G<u>A</u> | G | G | <u>A</u> | G<u>A</u> | G | Sanger |
| 70246957 | 26190 | Intron 6 | A | A<u>G</u> | A | A | <u>G</u> | A<u>G</u> | A | Sanger |
| 70247901 | 27134* | Intron 7 | T | T<u>G</u> | T | T | <u>G</u> | T<u>G</u> | T | Sanger |
| 70248473-4 | 27706-27707 | Exon 8 | AT | AT/<u>delAT</u> | AT | AT | [<u>delAT</u>] | AT/<u>delAT</u> | AT | Sanger |

*g.27134T>G, HypCH4III RFLP, AJ: Ashkenazi Jewish, AA: African American; last two rows represent the g.27134T>G and g.27706_27707delAT; variant residues are underscored From the foregoing it will be appreciated that, although specific embodiments of the invention have been described herein for purposes of illustration, various modifications may be made without deviating from the spirit and scope of the invention.

---

What is claimed is:

1. A method of determining the copy number of a SMN1 gene and detecting microsatellite alleles in a subject, the method comprising:
   (a) obtaining a DNA sample from the subject;
   (b) analyzing the DNA sample using multiplex ligation-dependent probe amplification (MLPA) to determine the SMN1 copy number in the subject; and
   (c) analyzing the DNA sample to detect the alleles present at least at three of four consecutive loci set forth as D5S681-D5S435-MS1-D5S610 in the subject's DNA.

2. The method of claim 1, wherein analyzing to detect the alleles present includes detecting alleles of D5S681, D5S435, and MS1, and optionally the alleles of D5610, and
   wherein the method further includes determining a haplotype for the subject at those alleles, and
   wherein the subject is identified as at risk of being a silent carrier (2+0) of Spinal Muscular Atrophy (SMA) when SMN1 copy number is two and wherein the subject carries a haplotype for D5S681-D5S435-MS1-D5S610 that is 2-5-6-10, 2-5-4-5 or 2-5-4-9, or wherein the subject carries a haplotype for D5S681-D5S435-MS1 that is 2-5-6.

3. The method of claim 2, wherein the haplotype for D5S681-D5S435-MS1-D5S610 is 2-5-6-10.

4. The method of claim 2, wherein the haplotype for D5S681-D5S435-MS1 is 2-5-6.

5. The method of claim 1, wherein analyzing to detect the alleles present includes detecting alleles of D5S681, D5S435, MS1, and D5610, and
   wherein the method further includes determining a haplotype for the subject at those alleles, and
   wherein the subject is identified as at risk of being a deletion carrier of Spinal Muscular Atrophy (SMA) when SMN1 copy number is one and wherein the subject carries a haplotype for D5S681-D5S435-MS1-D5S610 that is 2-1-4-5 or 2-5-4-5.

6. The method of claim 5, wherein the haplotype for D5S681-D5S435-MS1-D5S610 is 2-5-4-5.

7. The method of claim 5, wherein the haplotype for D5S681-D5S435-MS1-D5S610 is 2-1-4-5.

8. A method of identifying a subject with an increased risk of SNM1 duplication and an increased risk of being a carrier of Spinal Muscular Atrophy (SMA) comprising:
   (a) obtaining a DNA sample from the subject;
   (b) analyzing the DNA sample using multiplex ligation-dependent probe amplification (MLPA) to determine the SMN1 copy number in the subject;
   (c) analyzing the DNA to detect the alleles present at each of D5S681, D5S435, MS1 and D5S610;
   (d) detecting in the DNA sample the presence of a haplotype selected from the group consisting of
      (i) a haplotype comprising D5S681 having allele 2, D5S435 having allele 5, MS1 having allele 4, and D5S610 having allele 5;
      (ii) a haplotype comprising D5S681 having allele 2, D5S435 having allele 5, MS1 having allele 9, and D5S610 having allele 4;
      (iii) a haplotype comprising D5S681 having allele 2, D5S435 having allele 5, and MS1 having allele 6; and
      (iv) a haplotype comprising D5S681 having allele 2, D5S435 having allele 5, MS1 having allele 6, and D5S610 having allele 10;
   wherein the presence of two copies of SMN1 and the presence of the haplotype identifies the subject as having an increased risk of SMN1 duplication and an increased risk of being a carrier of SMA.

* * * * *

UNITED STATES PATENT AND TRADEMARK OFFICE
CERTIFICATE OF CORRECTION

Page 1 of 1

PATENT NO. : 9,994,898 B2
APPLICATION NO. : 14/122871
DATED : June 12, 2018
INVENTOR(S) : Lisa Edelmann et al.

It is certified that error appears in the above-identified patent and that said Letters Patent is hereby corrected as shown below:

In the Claims

At Column 59, Line 22, "D5610," should be -- D5S610, --.

At Column 59, Line 37, "D5610," should be -- D5S610, --.

At Column 59, Line 42, "one" should be -- one, --.

At Column 60, Line 16, "SNM1" should be -- SMN1 --.

At Column 60, Line 37, "10;" should be -- 10, --.

Signed and Sealed this
Twenty-sixth Day of February, 2019

Andrei Iancu
*Director of the United States Patent and Trademark Office*

SEQUENCE LISTING

<160> NUMBER OF SEQ ID NOS: 24

<210> SEQ ID NO 1
<211> LENGTH: 28072
<212> TYPE: DNA
<213> ORGANISM: Homo sapiens

<400> SEQUENCE: 1

```
ccacaaatgt gggagggcga taaccactcg tagaaagcgt gagaagttac tacaagcggt      60
cctcccggcc accgtactgt tccgctccca gaagccccgg gcggcggaag tcgtcactct     120
taagaaggga cggggcccca cgctgcgcac ccgcgggttt gctatggcga tgagcagcgg     180
cggcagtggt ggcggcgtcc cggagcagga ggattccgtg ctgttccggc gcggcacagg     240
ccaggtgagg tcgcagccag tgcagtctcc ctattagcgc tctcagcacc cttcttccgg     300
cccaactctc cttccgcagc ctcgggacag catcaagtcg atccgctcac tggagttgtg     360
gtccgcgttt ttctacgtct tttcccactc cgttccctgc gaaccacatc cgcaagctcc     420
ttcctcgagc agtttgggct ccttgatagc gttgagtgga ggccctgccg cgacttggca     480
gtagcttatt ttgttcactc ctctctggct ggtgtggggg aggtgggggc attaggccag     540
ggtgaagcag gggaaccact taggagtctg ttaagatgat ctgaacttca gaacaagatg     600
ttattaacag agtgaaagta tttggattct gggtatattt tgaaatcgga ggcaacaggt     660
ttttcagata gattcgataa cggaggttat cctgaatagt tgaaaagata agttgccttt     720
ttgctgaggt gggaaagaga agattgccag tagagcaggt ttctcaggag ttcagtcttg     780
ggcatagcat ggtaggggtg aatttggctg gagtgagttg gagagtagga gaagagaaat     840
ccaaggcaac atttgaccag cctgggcaac atagtgtgac tccgagtctg caaaaattag     900
acgggtgttg tggtgcgcgt ctgtggtctc agctacctgg aaggttcagg ccttggaagg     960
ctcagggagg tggaggctgc agtgatctgt gattgcgcct ctgcactcca gcctgggcga    1020
cagagccaga ccctgtctta aaacaaaata aacggccggg cgcggtggct caagcctgta    1080
atcccagcac tttgggaggc cgaggcgcc ggatcacaag gtcaggagat cgagaccatc    1140
```

```
ctggctaaca cggtgaaacc ccgtctctac tacaaataca aaaaattagc cgggcgtggt    1200
gacgggcgcc tgtagtccca gctactcggg aggctgaggc aggagaatgt catgaagccg    1260
ggaggcggag cttgcagtga gccgagatcg cgccactgca ctccagcctg ggcgatagag    1320
caagactccg tctcaaataa ataaataaat aaataaataa ataataaaaa catcggtagg    1380
catatttcaa ggaattctat ttaaaaaaaa tttttttaga gacaagttcg ctctctgtgg    1440
cccaggctgg agtacagtgg catgatccta gcccatggca gcgttgatct cttggcctca    1500
agcgaccctc ctttggagtc gctgggccta aaggagtgag ccaccacgaa atttattat    1560 aaatggaggg tagagaaatt gggcaataaa tggagggga agtgagttaa gaggaatttt    1620
aattatgtgt gtgtggtttt aaagagggg ggtcttgctc tgttgcccag gctgctgggg    1680
tgccagtggc gcaatcatga atcactacag ccttggactc ctggcctcaa gctatcctcc    1740
cacctctgcc tcccaaagta ctgggattac tagtgtgagc cactgcacta agataggagc    1800
aacatgtttc agcatgtttg tgggttgata ggaaagatga aatgggaaa gttgatgtcg    1860 gaaagaagac aatggctaga gcaatgtcct agagtaggta agaagggatg gatttggcct    1920
ttgttggaaa cattagcggt tcttttggtg acagctatat agttaacaca tctatgatac    1980
gtgaatggga agataggatg gcaggagatt ttgaaagttc tcttgattct tactgttctc    2040
ttagtgaaag aagcaaggtt atcagctaga agctgggatg ggagaggaaa gagaagatgg    2100
gaagtagata gttctttaga agagtgggca agggttggac tagggaagtt tagtggaaat    2160
attgctaggc aacataaaga gcctacttga gattcgtggt catgagttga aggagaccag    2220
acagcaagat tgtgtatgag ggcacccaca gagtaaatgg agagttgaaa ttaatgcagt    2280
tgtgatttta ccacgtggat atgaagaagt gaggggaga agtacaaagg agttctctta    2340
atgattgacc atggaattta agctggctaa gaaaggaagt gagaggccgg gcgcggtggc    2400
tcacgcctgt aatcccagca ctttgggaga ctgaggtggg tggattacct gaggtcagga    2460
gtttgagacc aacctggccg atatggcgaa accccatctc taataaaaat acagaaaaat    2520
tagccgggaa tggtggcagg tgcctgtaat cccagctact caagaggctg tggcaggagt    2580
atcccttgga cccaggaggt ggaggttgca gtgagccgag atcacgccac tgtactccag    2640
cctggacgat atagtgagac ttcacctcaa aaaaaaaaa aaagaaagg aagtgaggat    2700 tttaagaccc tgagagacag tttaaaaagt gggaggatcg gccgggcgct gtggctgaca    2760
cctgtaatcc cagcactttg ggaggccgag ttgggcagat cacaaggtca ggagttcgag    2820
accagcctgg ccaatatggt gaaaccttgt ctctactaaa aatacaaaaa ttagccgggc    2880
atggtgtcac gtgtctataa tcccagctac tcggaggct gaggcagaaa aattgcttga    2940
acctgggagg cagaggttgc agacagctga gatcactcca ttgcactcca gcctgggcaa    3000
caagagcaaa actttgtctt taaaaaaaaa aaaaaaaaaa gaatacaaaa attagccggg    3060
cgtggtggcg cgtgcctata atcccagcta cttgggaggc tgaggcagga gaatcagttg    3120
aacacgggag gcgaggtttg cagtgagccg agattgcgcc actgcactcc agcctgggcg    3180
acagagcagg actcctcttg gaaaaaaaaa attagctggg catggtggca ggtgcctgta    3240
gtctcagcta ctaggaggc tgaggcagga aaatcacttg aacccgggat gtggagtttg    3300
cagtgacccg agatcgtgcc actgtactcc atcctgggcg acaaaatgag actctgcctc    3360
aaaaaaaaaa aaaaaaaaaa aaaagtgggg aggatcaatg tactgccagt cctaatgaag    3420
tggaatgatt gtcccatca aatcactagt aggagtaagt tgcagagcct agaaggtgat    3480
ggttaagaga gtgggattct tgaaactgca tttatggaga ggttgtggtt attggttata    3540
```

```
ataaataaat acagttgaag tgagtgagta gctgagattt ggggatgtat cagttcattc    3600
ttacactgct acaaagacat acctgagacc aggtatttat aaagataaga ggtttaatca    3660
gctcacagtt ctgctgcctg tacaggcttc tcttgtggag gcctaaggaa acttacagtc    3720
atggtggaag gtgaagggga aacaagcaca gtcttcacat ggccagcagg agagagagag    3780 aaggggggaag tgctacatac tttaaaacaa ccagatcttg tgagaacgct tatcaggaaa    3840
cagcacttgg ggatggtgct aaatcattag aaatcacccc catgatccag tcgcctccta    3900
ccatgcccac ctccaacact ggggatcaca attcagcatg agatttgggt aggaacacag    3960
agctgcacca catcagagga tgtacaagat tgtggtggag aggagtttag agacctgcaa    4020
atatagggta attgaaggga tcatctacat ggatatttaa atcaccaaaa attatgacag    4080
gagtagtgtt ggagagagaa ctgcgatgta aacattaagg aatgaggaag agtgactcgg    4140
taggctgtag gtgactgcaa taggaaacga taatagactg tgagtctggt gacaagattt    4200
tccttctttc ttttttttccc cccccccgag acagggcctc tttttgttgc ccaggtggga    4260
gtgcagtggc gcgatcacgg ctcactacaa cctcctccca agctcaaggg attctcccac    4320
ttcagcctct caagtagctg gaactacagg tgctgaccac catgcctggc tactttttgt    4380
caggattttc aaggctggga attttgagag gggaatggag gagaataatc tgaaagtgca    4440
agtaaggagc agggaagatt tcttttttct tttttttttt tttttttgag tcggagtctg    4500
gctcagtcgc ccaggctgga gtgcagtggc gagatctccg ctcactgcaa gctccgcctc    4560
ccgtgttcac gccattctcc tccttcagcc tcccgagtag ctgggactac aggcgcccgc    4620
caccacgccc agctaattgt ttttttgtat ttttagtaga cggggttt caccgtgtta    4680 gccaggatgg tctcaatctc ctgactttgt gatccgccca ccccggcctc ccaaagcgct    4740
tgggattaca ggcgtgagcc accgcgccag ccagagcagg gaagatttct tccccacatc    4800
tccagtaggt acagtgatat gaagtgtgtg gaggagaaaa gaggaaacat ctatcatttg    4860
agatggctgc gaaaggaaaa ggcatcctca gggagctaga ttttacttag agcaagaaat    4920
gaagggatga ttcagaggtt aaaagagtgg atttttatgaa ttactcaagg gagcacagtg    4980
gaagtttcag gaagtggtag gagaaggtag aagatggcag ggtgttggga ataatttgag    5040
aaatctgagc tactggaaat gactgagaat cagatataaa ggcagtcctg gtggtccgtt    5100
ctggctgccg ttgctgtgta acgaatctgc caaaacttag tggcttgaaa caacaaagaa    5160
cattttatta tctctcattg tttctgtggg ttaggaattt gtgagagccg tgctgggcag    5220
ttttcgtgcg gctgtctcgt ggttgcacct acatagttgc tagagctaca gtagctgggg    5280
actgagcagc tagggattgg caggctatct cttttttca tgtagtctca tgaagatttc    5340
tttatgtggt ttcaatgtgt gggctggttt ggatttcctt atagcatggt ggcctcagtt    5400
ggattgctgt tttgtgatcc ttttcatccc tccttgtcct gtccccagac aaccactgat    5460
ctactttctg tcaccataga ttagcctgca tttttaagaa ttttatataaa cgtggaatga    5520 tagagtacct ttttgtcac gtttcttta tttatcatag ctatttgat tttcatccat    5580 tttattgctg agtagtatcc cattgcatgt atatactata ctgtattcat tcgcttgctt    5640
gtgaacattt gggcttttc cagttgggga ctgttaacaa gtagagccac tatgaatatt    5700
agtgtataag acttcatata gccaaggctg gcagatcgct tgagcccagg agtttgagac    5760
cagcctggga aacatggtga aacctctatt tttattttaa aatcaaaaat taaaatttt    5820 ctataaaaaa ttttaaagaa gactttgtat agacatacgc tttcatttt cttgagtgaa    5880
```

```
tacttaggtc tcagggtaga tgtattttaa gtctttaagg agctgtcaaa ctcttcctca   5940
aagtggtggt tgtaccatgt tactttttaa tataacagag attaattgag caaagaaaaa   6000
ttcaaaagtt ggacagcccc cacaactaaa taggttcaga acagctcccc cattttgcat   6060
tttgaccagc aatgtatgaa agttccattt gctcagtgtc cctgcaaaca cctggtatgg   6120
tcagtctttt taattttagg cattataata gatatagtgg cttcttgtga ttttaattag   6180
catttcctaa tgaccagtgc tgctgttgat catttcatga gtgtatttgc catccgtata   6240
tcttttttgg tgaagtgtct attcaaatca tttgggtttt ttttttttt gttttttttt   6300 tttggagaca gtgtctcact ctgtcaccca ggctgttgtg cagtggtgca atcacacagc   6360
ctactgcagc ctccacctcc tgcgctcagt cttcttgtct cagccttctg agtagctgaa   6420
attacgagca cacgccacaa tgcctggcta attttttaaa attttgtaga aacaaggtct   6480
cattatgttg cctgggcttg tcgtgaactc ctgggctcaa gcaatcttcc tgcctcagcc   6540
tcccaaagat tgggattgca agtatgagcc actgcacccg gccaacttac ccatcttta   6600 attgaatttt tttgttgttg aggttgaga gttcttcatg tttgctgggt acaatatctt   6660
tatcagatag gtaacttgca tgtattttct cccggtttac actttggttt tcattttgt   6720 taacaacgtc ttttaagaa cagaaaatct taattttgct gaaatctaat ttttcagttt   6780
tttctttgat ggttttgaga gaggaggtaa aaaagacta ggtaagccga tagttagaca   6840
gagtcctcgg tagaacttcc cttctaacaa aaagcagccc aagaaatcac ttctcttcta   6900
acaaggagca gcctggaaga tcgggctgta acatgtata aggaagcagc tctggcacag   6960
agggggagct tcctgggtaa tcagcaagct tcacatacgt aaggtgggta tgtgaagtaa   7020
acacagtatg tgaagtaaac acagtggacc ttagtacata ctcagataag gaagctggaa   7080
gcttgcatgt tgtgagttgt tggggttgcc tgcagctgca cggagagaaa ggggtacctg   7140
gggccaggca tgtccaccat ggtggctcca cctcccctta tttagcacat gcacaatagg   7200
aaagagataa gcaatgtgga gtagctcagg ccaaggacct gcctgcataa taaaaggttg   7260
gggtggggga tgccagagat tcacgctctg tgcagatggc aacacctggt cctaactggt   7320
tttttgctcc ctatgtgtag ataagctacc cccttcccat tagctcattt ataaaaatgc   7380
ttgcatttca ctgtggaatg ggaactcttt tcaggacctc tctctgcagg agagagctag   7440 tctcttctt ttgcctatta aacttctgct ctagcctcac accttggtg tgtcagcgtc   7500 cttgatttcc tcagcgtgag accaagaacc tcgggtgcca ccccaggcaa caaggccatt   7560
tcagtttgtt ctttgttat aggcaatcca tgatcacaga ttttctctc tttttttttt   7620 ttacacagtt tagagtttta gttttacact taggtctgta atccattttg tattaattct   7680
tatatgtggc tcagtgtagg tggaaatttg gtttgttttt gcataaggat ttccaatagt   7740
tttaccacca tttcttgaaa ctactatgct ttctctatta aaccacattt gtaactttag   7800
ttaaaatcag tcacatatat cacagggcta tttctgactc tcaattctgt tacattgtct   7860
attagtgtat attgatgtca gtactacact tttaattact attgcttcag ggtatgtctt   7920
gtaaaccaaa aataaaatta taggcccccc ccgcccctgc acaaccaact gaatggaccc   7980
atcctctcag ccaagggcat tccaaaatta acctgaaaaa ctagttcaag ccatgatggg   8040 aaggggagt tggacatgtc tcatcacacc ctactacctt ttggaattac tgatagaaca   8100
gactcttaaa gtctgaaaag aaacatttac aacctaccct ctctgaagcc tgctacctgg   8160
gagcttcatc tgcatgataa aaccttggtc tccacaaccc cttatggtaa cccaaacatt   8220
cctttctgtt gataataact ctttcaacta gttgccaatt agaaaatctt taaatcttcc   8280
```

```
tatgacctag aaacctccct accccccactt tgagttgtcc tgcctttcct gacagaactc   8340
atgtacatct tacatatatt gattgatgcc tcatgtctcc ctaaaatgta taaaacaaag   8400
ctgtacccca ccaccttggg gacatgtcat caggacctcc tgtggctgtg tcataggagc   8460
gtctttaact ttggcaaaat aaactttcta aattgattga aacctgtctt agctacttct   8520
ggtttacagt cttaaagtta gataatgtaa attgtccagc tttggtttat ttttgtcctt   8580
agtagttcca tataaatttt agaatcagct tttcaattta atacactact ttcctcttag   8640
atccacaatt aaatatattt gatgctaaca attctgtttt atgttttcg tttttttttt    8700
ttgagacaag agtttcgctc ttgttgccca ggctggagtg cagtggcgcg atcttggctc   8760
accacaacct ccacctccca ggttcaagca attcttctgc ctcagcctcc cgagtagctg   8820
ggattacagg catgcgccac cacgcccggc taattttgta tttttagtag agacggggtt   8880
tcaccatgtt gatcaggctg gtcttgaact cctgacctca ggtgatccac ccacctcggc   8940
ctcccaaagt gttgggatta caggcgtgaa ccaccatgcc tggccagttc tgttattttt   9000
aaaacccaag tttccctggt catatcttgg ttggatgaag cgtattttca atagattacc   9060
ctggaaaggc tagtgagtac ggtattcttc tacattttag acttttctta gtcttgctac   9120
ttcaaggaca gctaggctgc atataaaatt cttggctcat acttttccc cataaatttc    9180
tatgagaaag tctaatgata actgattttc tttattttgt aacttagtct ttttgcttag   9240
aggctctctg aggatgggag ggggttcttc ctcccatccc taggaatttt tctttttttt   9300
aaattcctaa tcactagacc accaggaaga ttgtttgttt tgttttgttt ttattcttca   9360
gggacccat ttatacatac gttaaataaa tactgtttgc caatgtatca accattttgc    9420
ttcttattta ttttttgttcc tttggttctt tttcatggct ttgctttggt gctccttaga   9480
ttttcagtca gatgtatttg tccttgggta ccttgtaatc agtattacct tttcttctgt   9540
cgctttgttt tctgttcgtt ttgaaattac ttgtttcctg gtctggcaat aacagttgag   9600
atatgaggag tttgagctgc catctgtcta tgtatcttgc tttaagactg cactcttcta   9660
ttgatatcac tggccttgat tttgtgattt ctttatttct tcaggaccac ccttcatttt   9720
ctactgtttg cttcctttt ttttgagatg gagtctcact ctgtcactca ggctggagtg    9780
cagtgatctt ggctcattgc aacctctgcc tcccgggttc cagcaattct cctgcctcag   9840
cctcccaagt atctgggact acaggtgtgc accaccatgc ccggctaagt tttgtatttt   9900
taatagagac ggggttttgc cacattggca ggctggtctc aaactcctga tgtcaagtga   9960
tccacccacc ccacccacct ctgcatccca aagtgctggg attacaggaa tgagctgccg  10020
tgcccagcct ccccccctacc ccccttttt tctttcgaga cagagattat aggtgtgagc   10080
cactggaccc agcctgtttt tattcctttt accaaatctc caaggaatat cttcccttcc  10140
aagtgcgaat gtaaccttaa gtcagttaac ctctttgtga ttacttttct tatctgcaaa  10200
gtgacttaat gatcttaagt acttttttt tttgagacag ggtctcactg tcaccctggc   10260
tggagtgcag tggcacgatc tctgatctcc actcactgca atctcctctt ccctggttca  10320
agcggccctc ccaccttagc cttctgggta gctgggacta cagatgtgaa ccaccacgcc  10380
cagctaattt ttgtactttt tgtagagatg gggttttgcc atgttgccca ggctgggatt  10440
attaagtact ttttatcata cagcaagatt gacattttat attggaatac atttgtctct  10500
atataacgga gattaacagg aaaatgacaa gcctgggtgc ggtggctcat gcctgtaatc  10560
ccagcacttt gggaggctga ggtgggagga tcacttgagg tcaggagttc gagaccagtt  10620
```

```
ttgccaagat gatgaaagcc catgtctact aaaaatacaa aaattagccc agcttgatgg   10680
tgggcgccta taatcccagc tatttgagag actgaggcag gagaatcact tgaacctggg   10740
cggcagaggt tgcagtgagc cgagatcatg ccactgcact ccagcctggg tggcatagcg   10800
agactcttgt ctcaagagaa acaaaacaa aacaaaaaaa aaacaggaaa atgacaaaaa   10860
gtaatattac aactcagtga attttataac aaactttttt ggaattcatt gactaatact   10920
ataccaaatc caaaatactc tctagtatac caaatccaac tctaccctat agtataaatt   10980
ggattctatt tggacttgtc tcactaatcc ctcatacagt gtgttttatt ttttattgaa   11040
gtaaaaaaat ttgtcatttt aaccattttt aagtatatag ttcagtaata ttaagtatgt   11100
tcatgttgtt gcgcaataga tcttcggaag ttttttcgtct tgcaacctga aactctaccc   11160
attagcaaat tcccatttct ccttacactt agcccttggt aatcatcatt cttttttttt   11220
tttttttgag atggagtttt actcttgttg cccaggctgg agtgcaatgg tgcaatctcg   11280
actcaccaca acctccgcct cccaggttca agcaattcta cctcagcctc ccgagtagct   11340
gggattacag tcatgcacca ccacgcccgg ctaattttgt attttttagta gagaagggggt   11400 ttctccatgt tgaggctggt ctcgaactcc tgacctcagg tgatctgccc acctcggcct   11460
cccaaagtgc tgggattaca ggcgtgagcc actgcgcctg gcccattctt tctaattcta   11520
taaatttgac tacttagtta ccttacataa ataaattctt atagttagtg ttatttttgc   11580
ttccatgcct tttttgttgt tgttcatgct cttacttgga atgcgttcta ttttgtctac   11640
ctatgcacat cctgttgggt tttttttttt tttgggggtt ttttttgttt ttttttgttt   11700
ttttttccca gacaaggtct caatttgtta cccaggctgg agtgcagcgg cgccatctcc   11760
actcactgca tcctcaactt cctgggccca ggtgatcctc tcgcctcagc ccctgcaggt   11820
agctgggact ataggcatgt gccaccatgc ccagctaaat ttggttttttt tgtttgtttg   11880 tttttgagac agagtctcac tctgtcaccc aggctggagt gcagtggcac aatctcagct   11940
cactgcaatc tctgccgccc gggttcaagt gattctcctg cctcagcctc ccaagcagct   12000
gggattacag gtgactgcca ccacgccagc taagttttgt agttttagta gagatggggt   12060
ttcaccttgt tggccatgct ggtctcgaac tcctgacctc gtgatctgcc tgcttctgcc   12120
tcccaaagtg ctggaattac aggcatgagc caccacgccc ggccagaatt tttgtatttt   12180
tagtagacac aaggttctta ccctgttgcc taggctggtc tggaagtcct ggactcaagc   12240
aattcacctg ccttggcctc ccaaaatgct gggattacaa gccaccatgc ccggcctaaa   12300
tcctgttgtt ttgttttgtt ttattttgtt ttgttttgtt ttgttttgttt tttgagacag   12360 agtctcgcta tgtctctcag gctgtagtgc agtggcgcga tcttggctca ctgccacctc   12420
tgcctcccag gttcaagtga ttctcctgcc tcagcctccc aagtagctgg gattacaggc   12480
atgtgctact atgtccggct aattttttgta ttttttagtag acagggtt tcaccatgtt   12540 ggccaggctg gtctcgaact cctgacctcg tgatccaccc acctcggcca cccaaagtgc   12600
tgggattaca ggcgtgagtg gttttatttt cttaggccgg tttcctccat atgatcttgc   12660
agtagacatt aatttctttc cttttttaatt aaaatactgt tgtatttca cattttgatg   12720 tttgttaaga tttgttttat attgtttttt gttttgtctt gtgtgatagt cttaaatccc   12780
tagttagata ataactggag agtaccatgt ttctatatat ctctcagtga cttgcacagt   12840
gctagcagat agtgctaaaa aattatttat tattattatt attttgttat tgttgttgtt   12900
gttgttagac agggtcttcc tctgtcaccc aggctagagg gcaatgggat gatcatagct   12960
tactgcagcc tccaacaact gggctcatgt aattctcctg cctcagcttc ccaagtagct   13020
```

-continued

```
gggattacag gcatgagcca ccatgtctgg acaaaaatat ttccaggtgc agtggctcat   13080
gcctgtaatt cccacacttg ggaggccgag cgaggctgga ggatcacttg agcctaggag   13140
ttcaagacca gcttggctaa gatggcgaga ccccgtccct acaaaaaatt ttaaaaacta   13200
gccaggcatg gtggcatgca cctatattcc caactactca gtgggctgag gtgggagggt   13260
catttgaaca caggaatttg aggggagaaa aaagaagag agaaagagaa gtgaaggaag   13320
gaagaaagga aggagggagg gagagaagaa agaaacgaaa gaaaggaaaa gaaaaggaag   13380
gaaagaaaat tggtaccagg aaagcaggaa agggaaatgg aagtaaaaaa ataataataa   13440
taataaaatg aaaattggtt agtcactatt aacaatttgt atccttataa tctggaaaca   13500
ttataatttc aaaagaaaaa atattctttg gatcataggt tctgaggtca gaacagcatt   13560
cccgtagtct agatgaagtc aagttttatc tgatcttaat tgaaataaat atagctggcc   13620
ttgaacaaat ctactcatgg tatgtggata ggaattaaat tgtagggca ttcacttgat   13680 ggcattcatt cttagaacat ttacctatgt ctagcttttg gagtaaagtc acataacctc   13740
taaccaggta agtttcctgt ggctttattt aggatttttaa atactcattt tcagtgtaat   13800
tttgttatgt gtggattaag atgactcttg gtactaacat acatttttctg attaaaccta   13860 tctgaacatg agttgttttt atttcttacc ctttccagag cgatgattct gacatttggg   13920
atgatacagc actgataaaa gcatatgata aagctgtggc ttcatttaag gtatgaaatg   13980
cttgcttagt cgttttctta tttctcgtt attcatttgg aaaggaattg ataacatacg   14040
ataaagtgtt aaagtacatg ttattcagtt tcattttga agattagatg gtagtatgag   14100
ttagttaaat caggtgatat cctcctttag aagttgatag cctatatatg tcatcctttg   14160
tggaggcaat ttaaataaaa tttaaaacat ttattcctgg ctgggtatgg tggctcactc   14220
ctgtaatccc agcactttga gaggctgagg cgggtggatc acctgaggtc aggagtttga   14280
gaccagcctg gccaacatgg tgaaacccg tctttactaa aaatacaaaa attagccaag   14340
catggtggca cgtgcctgta atcccagctg cttgggacac tgaggcagga gaattgcttg   14400
aacctggggg gcagaggttg caatgattgc accactgcac tccagcctgg gcgatagagt   14460
gagactccat ctcagaaaac gaacaaacaa tgtattcctt ttagtatttt tacattgtat   14520
caaactatgg aagtcctcta attgagatta ataagaaaaa gacaatctga attataattt   14580
taaacattta acaagcatgt agtaaaataa tgatgaagat aaatagcatt agtacagcaa   14640
ttaatatttg tagcatgctg acagtgctct gtgtgcgttt catatattaa attactctaa   14700
tcatcccaaa tcctgtaagt tgggtatcaa ttcaagtgtt cctattgggt aggaatatac   14760
agttctttta ggaaatgtag tatggttctg tgtctcaaac aggacactta cacagttggc   14820
caacatcatc accttctcca ttctctgaga tgtttagtct tactgagcac taaatatggg   14880
tcatcaatag tccagactac cttgagcaaa caatagtcca gactaccttg agcaaacaga   14940
gcatatactc atacagtgta taagagcac caagcataca gatttcatgt ctttctcata   15000
gttactcttg taacatgagc taaagatcag acctctatgt caccttttgta actgatttct   15060 agattttttt ttttttttga gatggggtct tgccctgtca cccaggctgg agtgtagtgg   15120
cgtgatcatg cctcattgga gccttcaact catgagctca aacaatcctc ctacctcagc   15180
ttcctgagta gttgggacca caggtgtgtg ccaccacacc cagctcattt ttgtattctt   15240
tgtagagatg cagtctcacc ctgttgccca cgctggcctg gaactcctga gctcaaaaga   15300
tccctccgcc ttgaccttcc aaagtgctgg gattacaagc atgaaccact gcacccggcc   15360
```

```
tagatttta  aatgtgcttt  ccagtataca  ctgaaactag  aagtcgacta  aagaattacc   15420
aagagaattc  tataaaatag  agattgaaat  ggggctcgat  gtgggatggg  ttggtgatat   15480
tgcagggaga  agtaatctga  gtaaaggagg  aaaagaactg  atttgggaaa  acgatagttt   15540
tagtagtgag  tttgagtatg  aattaagttg  agattgaatt  tgaattaagt  tgaggttgaa   15600
tatgaattaa  gttgaggttg  agtttgaggt  atgaattaag  atgtgaaatt  gatcattgga   15660
aatgttagat  tgagaaaagt  cacagctgga  ttaatagctt  cagaagtgtg  tttgcagaca   15720
gttgcaacta  aagtaataag  aatagatggc  cttggccggg  cgcggtggct  cacgcctgta   15780
atcccagtac  tttgggaggc  tgaggcgagc  aaatcacgag  gtcaggagtt  caagaccagc   15840
ctggcccaca  tggtgaaacc  ccgtctttat  aaaaatacaa  aaattagct  gtgcacagtg   15900 gtgcacgcct  gtaatcccag  ctactcggga  ggctgagaca  ggagaatcgc  ttgaacctgg   15960
gaggtggagg  ttgcagtgag  ctgagatcag  tgtgactgca  ctccagcccg  gtgacagagt   16020
gagactctgt  gtaaaaaaat  aaataaata  aataatggc  cgtaagcaag  taaagaagga   16080
tggccagctc  ttattgggaa  tgcctaaatc  taaggcttga  tcagaagtaa  tgaaaccgtt   16140
ggggccctac  attgctatga  catccaaagg  gccatgaata  tcaggaagaa  agataattaa   16200
cagggtctaa  tgttacagag  aggttgagag  caaggagatt  tgattaaaag  ggtctttaga   16260
gctgatgtca  ggtgtatgat  gcctttaaga  gcagtttta  tagtgcaggg  ggtggtcaaa   16320
agagaaaata  ggtgctttct  gaggtgacgg  agccttgaga  ctagcttata  gtagtaactg   16380
ggttatgtcg  tgacttttat  tctgtgcacc  accctgtaac  atgtacattt  ttattcctat   16440
tttcgtagca  tgctctaaag  aatggtgaca  tttgtgaaac  ttcgggtaaa  ccaaaaacca   16500
cacctaaaag  aaaacctgct  aagaagaata  aaagccaaaa  gaagaatact  gcagcttcct   16560
tacaacaggt  tattttaaaa  tgttgagatt  taacttcaaa  ggatgtctca  ttagtcctta   16620
tttaatagtg  taaaatgtct  ttaacttaag  tgattagtac  agtgtttcta  ttgacatata   16680
cttatacaac  ttcaaaaaca  actattaaat  tttctgttat  ttaggaacat  gcatattagt   16740
catgaaagta  taaagaatta  gatgggaatg  ataaatgcta  aaatcaggac  atgtgttcca   16800
tttgtgaatg  gaaggcaggg  agaaggtgcc  gtttggaagg  agtacccaag  agccgtaagc   16860
tgaattggca  gtgttttaca  tcttaagctg  agagatagat  ttttttttcc  cctttttctt   16920
taaaaactct  aaaactgtta  attccaagga  acccagaagt  ctaggtagat  tatttctgct   16980
agttaaaagc  agtagtcctg  aaagctgaat  attttggtgt  cttttgagcc  aactttagtt   17040
tcatcattac  caaggggaa  gagagctaac  agttgatgag  cacttgctct  aggccagtcc   17100
agagtgctgg  gcaccatacg  cattttatct  ccctcccgct  attcacaaca  aatatgggag   17160
gtagtttata  ttatagccat  ctaataagat  ggggaaacta  agactcaaag  agattcagaa   17220
acttgtccat  gattataaat  gtaagagagt  tggaattcag  atttatgtat  ttagacccca   17280
agcctttctc  attacatcat  tttgccttcc  aaatctctac  cctctatcct  tcacctcccc   17340
actgatcaaa  acgagatgat  agtttgccct  cttcaaaaga  aatgtgtgca  tgtatatatc   17400
tttgatttct  tttgtagtgg  aaagttgggg  acaaatgttc  tgccatttgg  tcagaagacg   17460
gttgcattta  cccagctacc  attgcttcaa  ttgattttaa  gagagaaacc  tgtgttgtgg   17520
tttacactgg  atatggaaat  agagaggagc  aaaatctgtc  cgatctactt  tccccaatct   17580
gtgaagtagc  taataatata  gaacaaaatg  ctcaagaggt  aaggatacaa  aaaaaaaaa   17640 attcaatttc  tggaagcaga  gactagatga  gaaactgtta  aacagtatac  acagttgtca   17700
gtttgatcca  ccgaggcatt  aatttttct  taatcacacc  cttataacaa  aaacctgcat   17760
```

```
attttttctt tttaaagaat gaaaatgaaa gccaagtttc aacagatgaa agtgagaact   17820
ccaggtctcc tggaaataaa tcagataaca tcaagcccaa atctgctcca tggaactctt   17880
ttctccctcc accaccccc atgccagggc caagactggg accaggaaag gtaaaccttc   17940
tatgaaagtt ttccagaaaa tagttaatgt cgggacattt aacctctctg ttaactaatt   18000
tgtagctctc ccatgaaact tttgtagctt aaatacacaa gaattttttg aaaaggaaat   18060
aagataatga tgcaaaatag ttaatttttt aaaaaaatgt tagacactgc agtggatgca   18120 acaaatact ttatatgaaa gatttatcca gttaactttt gtggagtatt aggtattaga   18180
ctaataatta gcacacttac ttaagttaga aagtataata atgcgccgga cgcggtagct   18240
cacgcctgta atcccagcac tttgggaggc caaggtgggc ggatcacaag gtcaggagat   18300
cgagaccatc ctggctaaca cggtgaaacc ccatctctac tgaaaataca aaaaatttg   18360 ccgggcgtga tggcgggcac ctgtagtccc agctactcgg gaggctgagg caggaggatg   18420
gtgtgaaccc cggaggcaga gcttgcagtg agtcaagatc gtgccactgc actccaacct   18480
gggcgacaga atgagactcc atctcaaaca aaaaaacaaa acaaaacaaa aaaaagtgta   18540
ataataattt atcattagct ggatgatatg ctgttgtttc ccatgtcacc tgtataagat   18600
atgtaaaata agaacacatt atttacatct aatatagata aaatcctgag gcgctctcag   18660
attgttttgt agagttcaaa tgtaaatatt gttttcattt atggtccttt tggttataag   18720
taacagaaat caactctaaa aagattttta ttataggtta gattatgtca tggaacctta   18780
aggcttgtcc ctttctagtt cttttgtgta aagcggtgat ttcttccatg gagggaatgg   18840
tatttaggca atttttttt tttttcgaga tggagtcttg ctctgtcgct caggctggag   18900
tgcagtggca ccatttcagc tcactgcaac ttccacctcc tgggttcaag tgattctcct   18960
gcttcagcct cccaagtagc tgagattaca ggcacccgcc accacacccg gcttattttg   19020 tattttagt agagatgggg tttcaccatg ttggccaggc tggtcttgaa ctcctgacct   19080
caagtgatct ccccaccttg gccttccaaa gtgctaggat tacaggcgcc tagcctaggc   19140
agtcattttc aaaaaacaag catgactcac caaaagtttt aagattttct gtgataatgt   19200
tcttattgag gcttacatta tattacagtt tcttgaatct aaaatgatgt accctcttag   19260
gatatataca tcatgcttca ttggtctcag ggggctgatt tttataagga gagatttgct   19320
agttttcaca atatgtcctc taagttggca tgtatagcta aacaggcttt cataaaaata   19380
tacaatttag ttaatgaaat tgggatata gtcttttatg attgaaataa ttttgctaaa   19440
tagactgtct ctgatttatt aggtaatcac cactcttatt ttgttttact tccttaatgt   19500
ctacatagaa aggaaatgag aaaaatccag aggttgtcat ttgacttatg agtctgtttg   19560
acttcaggat ttggtacatg aaatttcact taatctttt gatatgtata aaacaaatat   19620
tctgggtaat tattttatc cttttggttt tgagtccttt ttattcctat catattgaaa   19680
ttggtaagtt aattttcctt tgaaatattc cttatagcca ggtctaaaat tcaatggccc   19740
accaccgcca ccgccaccac caccacccca cttactatca tgctggctgc ctccatttcc   19800
ttctggacca ccagtaagta aaaaagagta taggttagat tttgctttca catacaattt   19860
gataattagc agaatagagg attgtaaaat gtcattgtag aacatccctt gggccagatt   19920
ctaatgggta gaaatttgaa ctaaacctct gggttttgtt tgtttttaat gcctttctgt   19980
tacccagatg cagtgctctt gtagtcccaa gtcaagctc taggttgcct tctttcctgg   20040
cagaagttgg tgtctatgcc ataaggaggt agttcctgtt agaagggatt taattatacc   20100
```

```
ttatataagg aattagtgtt tgcccttcta ggtatagttg gatgttagct tctgatgtaa    20160
actggatttc ttttctcttc tctctctttt ttttttttg ttttggaggc agagttttgc    20220
ccttgtaccc caggctggag tgcagtggtg tgatctcagc tcacagcaac ctccgcctcc    20280
tgggttcaag caattctgcc tcggcctccc aagtagctgg gattacaggc gactgccacc    20340
acacccggct aattttttgtt ttattagtag agatggggtt tcaccatgtt ggccagactg    20400
atcttgaact cctgacctca ggtgatccac ccgccttggc ctcccaaagc gctgggatta    20460
caggcgtgag ctgccgcacc cagctgtaaa ctggatttct aatggtagat ttttaggtat    20520
taacaataga taaaaagata cttttttggca tactgtgtat tgggatgggg ttagaacagg    20580
tgttctaccc aagacattta cttaaaatcg ccctcgaaat gctatgtgag ctgtgtgtgt    20640
gtgtgtgtgt gtgtgtgtgt attaaggaaa agcatgaaag tatttatgct tgattttttt    20700
tttttactca tagcttcata gtggaacaga tacatagtct aaatcaaaat gtttaaactt    20760
tttatgtcac ttgctgtctt ttcgtcctcg ttaaatttaa ttttgttggt cttttgttgt    20820
tattggttgg ttttctccaa atgctagcta tgttaagaaa tttaaggcca ggtacagtgg    20880
ctcatgcctg taatcccggc attttagaag gctgaggcag gaggatcact tgagctcagg    20940
agtttgagac cagtctgggc aacatagcaa gacctcgtct tgtttaggg gaaaaaaaag    21000 aaatttaagt aggagattat ataagcaaaa atacaattaa tttccagcat tcactatata    21060
atataaatct ccagacttta ctttttttgtt tactggatat aaacaatatc tttttctgtc    21120
tccagataat tccccacca cctcccatat gtccagattc tcttgatgat gctgatgctt    21180
tgggaagtat gttaatttca tggtacatga gtggctatca tactggctat tatatggtaa    21240
gtaatcactc agcatctttt cctgacaatt tttttgtagt tatgtgactt tgttttgtaa    21300
atttataaaa tactacttgc ttctctcttt atattactaa aaaataaaaa taaaaaaata    21360
caactgtctg aggcttaaat tactcttgca ttgtccctaa gtataatttt agttaattt    21420 aaaaagcttt catgctattg ttagattatt ttgattatac acttttgaat tgaaattata    21480 cttttttctaa ataatgtttt aatctctgat ttgaaattga ttgtagggaa tggaaaagat    21540
gggataattt ttcataaatg aaaaatgaaa ttctttttt tttttttttt ttttgagac    21600 ggagtcttgc tctgttgccc aggctggagt gcaatggcgt gatcttggct cacagcaagc    21660
tctgccttct ggattcacgc cattctcctg cctcagcctc agaggtagct gggactacag    21720
gtgcctgcca ccacgcctgt ctaattttttt gtatttttt gtaaagacag ggtttcactg    21780
tgttagccag gatggtctca atctcctgac cccgtgatcc acccgcctcg gccttccaag    21840
agaaatgaaa ttttttttaat gcacaaagat ctggggtaat gtgtaccaca ttgaaccttg    21900
gggagtatgg cttcaaactt gtcacttttat acgttagtct cctacggaca tgttctattg    21960 tatttttagtc agaacattta aaattatttt attttatttt attttttttt ttttttgag    22020 acggagtctc gctctgtcac ccaggctgga gtacagtggc gcagtctcgg ctcactgcaa    22080
gctccgcctc ccgggttcac gccattctcc tgcctcagcc tctccgagta gctgggacta    22140
caggcgcccg ccaccacgcc cggctaattt ttttttattt ttagtagaga cggggtttca    22200
ccgtggtctc aatctcctga cctcgtgatc caccgcctc ggcctcccaa agtgctggga    22260
ttacaagcgt gagccaccgc gcccggccta aaattatttt taaagtaag ctcttgtgcc    22320 ctgctaaaat tatgatgtga tattgtaggc acttgtatttt ttagtaaatt aatatagaag    22380
aaacaactga cttaaaggtg tatgttttta aatgtatcat ctgtgtgtgc ccccattaat    22440
attcttattt aaaagttaag gccagacatg gtggcttaca actgtaatcc caacagtttg    22500
```

```
tgaggccgag gcaggcagat cacttgaggt caggagtttg agaccagcct ggccaacatg    22560
atgaaacctt gtctctacta aaaataccaa aaaaaattta gccaggcatg gtggcacatg    22620
cctgtaatcc gagctacttg ggaggctgtg gcaggaaaat tgctttaatc tgggaggcag    22680
aggttgcagt gagttgagat tgtgccactg cactccaccc ttggtgacag agtgagattc    22740
catctcaaaa aaagaaaaag gcctggcacg gtggctcaca cctataatcc cagtactttg    22800
ggaggtagag gcaggtggat cacttgaggt taggagttca ggaccagcct ggccaacatg    22860
gtgactactc catttctact aaatacacaa aacttagccc agtggcgggc agttgtaatc    22920
ccagctactt gagaggttga ggcaggagaa tcacttgaac ctgggaggca gaggttgcag    22980
tgagccgaga tcacaccgct gcactctagc ctggccaaca gagtgagaat tgcggaggg    23040 aaaaaaaagt cacgcttcag ttgttgtagt ataaccttgg tatattgtat gtatcatgaa    23100
ttcctcattt taatgaccaa aaagtaataa atcaacagct tgtaatttgt tttgagatca    23160
gttatctgac tgtaacactg taggcttttg tgtttttttaa attatgaaat atttgaaaaa    23220
aatacataat gtatatataa agtattggta taatttatgt tctaaataac tttcttgaga    23280
aataattcac atggtgtgca gtttaccttt gaaagtatac aagttggctg ggcacaatgg    23340
ctcacgcctg taatcccagc actttgggag gccaaggcag gtggatcacg aggtcaggag    23400
atcgagacca tcctggctaa catggtgaaa ccccgtctct actaaaagta caaaaacaaa    23460
ttagccgggc atgttggcgg gcaccttttg tcccagctgc tcgggaggct gaggcaggag    23520
agtggcgtga acccaggagg tggagcttgc agtgagccga gattgtgcca gtgcactcca    23580
gcctgggcga cagagcgaga ctctgtctca aaaaataaaa taaaaagaa agtatacaag    23640 tcagtggttt tggttttcag ttatgcaacc atcactacaa tttaagaaca ttttcatcac    23700
cccaaaaaga aaccctgtta ccttcatttt ccccagccct aggcagtcag tacactttct    23760
gtctctatga atttgtctat tttagatatt atatataaac ggaattatac gatatgtggt    23820
cttttgtgtc tggcttcttt cacttagcat gctattttca agattcatcc atgctgtaga    23880
atgcaccagt actgcattcc ttcttattgc tgaatattct gttgtttggt tatatcacat    23940
tttatccatt catcagttca tggacattta ggttgttttt attttgggc tataatgaat    24000 aatgttgcta tgaacattcg tttgtgttct ttttgttttt ttggttttt gggtttttt    24060 tgtttttgttt ttgtttttga gacagtcttg ctctgtctcc taagctggag tgcagtggca    24120
tgatcttggc ttactgcaag ctctgcctcc cgggttcaca ccattctcct gcctcagccc    24180
gacaagtagc tgggactaca ggcgtgtgcc accatgcacg gctaattttt tgtatttta    24240 gtagagatgg ggtttcaccg tgttagccag gatggtctcg atctcctgac ctcgtgatct    24300
gcctgcctag gcctcccaaa gtgctgggat tacaggcgtg agccactgca cctggcctta    24360
agtgttttta atacgtcatt gccttaagct aacaattctt aacctttgtt ctactgaagc    24420
cacgtggttg agataggctc tgagtctagc ttttaacctc tatcttttg tcttagaaat    24480 ctaagcagaa tgcaaatgac taagaataat gttgttgaaa taacataaaa taggttataa    24540
ctttgatact cattagtaac aaatctttca atacatctta cggtctgtta ggtgtagatt    24600
agtaatgaag tgggaagcca ctgcaagcta gtatacatgt agggaaagat agaaagcatt    24660
gaagccagaa gagagacaga ggacatttgg gctagatctg acaagaaaaa caaatgtttt    24720
agtattaatt tttgacttta aattttttt ttatttagtg aatactggtg tttaatggtc    24780
tcattttaat aagtatgaca caggtagttt aaggtcatat attttatttg atgaaaataa    24840
```

```
ggtataggcc gggcacggtg gctcacacct gtaatcccag cactttggga ggccgaggca   24900
ggcggatcac ctgaggtcgg gagttagaga ctagcctcaa catggagaaa ccccgtctct   24960
actaaaaaaa atacaaaatt aggcgggcgt ggtggtgcat gcctgtaatc ccagctactc   25020
aggaggctga ggcaggagaa ttgcttgaac ctgggaggtg gaggttgcgg tgagccgaga   25080
tcacctcatt gcactccagc ctgggcaata agagcaaaac tccatctcaa aaaaaaaaa    25140 ataaggtata agcgggctca ggaacatcat tggacatact gaaagaagaa aaatcagctg   25200
ggcgcagtgg ctcacgccgg taatcccaac actttgggag gccaaggcgg gtgaatcacc   25260
tgaagtcggg agttccagat cagcctgacc aacatggaga aaccctgtct ctactaaaaa   25320
tacaaaacta gccgggcatg gtggcgcatg cctgtaatcc cagctacttg ggaggctgag   25380
gcaggagagt tgcttgaact gagaaggcgg aggttgcggt gagccaagat tgcaccattg   25440
cactccagcc tgggcaacaa gagcgaaact ccgtctcaaa aaaaaagga agaaaaatat    25500 tttttttaaat taattagttt atttatttt taagatggag ttttgccctg tcgcccaggc    25560
tggggtgcaa tggtgcaatc tcggctcact gcaacctccg cctcctgggt tcaagtgatt   25620
ctcctgcctc agcttcccga gtagctgtga ttacagccat atgccaccac gcccagccag   25680
ttttgtgttt tgttttgttt tttgttttt tttttgaga gggtgtcttg ctctgtcccc      25740
caagctggag tgcagcggcg cgatcttggc tcactgcaag ctctgcctcc caggttcaca   25800
ccattctctt gcctcagcct cccgagtagc tgggactaca ggtgcccgcc accacacccg   25860 gctaatttt ttgtgttttt agtagagatg gggtttcact gtgttagcca ggatggtctc    25920
gatctcctga ccttttgatc cacccgcctc agcctcccca gtgctggga ttataggcgt     25980 gagccactgt gcccggccta gtcttgtatt tttagtagag tcggggtttc tccatgttgg   26040
tcaggctgtt ctccaaatcc gacctcaggt gatccgcccg ccttggcctc caaaagtgca   26100
aggcattaca ggcatgagcc actgtgaccg gcaatgtttt taaatttttt aaatttaaat   26160
tttatttttt agagaccagg tctcactcta ttgctcaggc tggagtgcaa gggcacattc   26220
acagctcact gcagccttga cctccagggc tcaagcagtc ctctcacctc agtttcccga   26280
gtagctggga ctacagtgat aatgccactg cacctggcta attttttattt ttatttattt   26340 atttttttt gagacagagt cttgctctgt cacccaggct ggagtgcagt ggtgtaaatc    26400
tcagctcact gcagcctccg cctcctgggt tcaagtgatt ctcctgcctc agcctcccaa   26460
gtagctggga ttagaggtcc ccaccaccat gcctggctaa ttttttgtac tttcagtaga   26520 aatgggttt tgccatgttg gccaggctgt tctcgaactc ctgagctcag gtgatccaac    26580
tgtctcggcc tcccaaagtg ctgggattac aggcgtgagc cactgtgcct agcctgagcc   26640
accacgccgg cctaattttt aaattttttg tagagacagg gtctcattat gttgcccagg   26700
gtggtgtcaa gctccaggtc tcaagtgatc ccctaccte cgcctcccaa agttgtggga    26760
ttgtaggcat gagccactgc aagaaaacct taactgcagc ctaataattg ttttctttgg   26820 gataacttt aaagtacatt aaaagactat caacttaatt tctgatcata tttttgttgaa   26880 taaaataagt aaaatgtctt gtgaaacaaa atgcttttta acatccatat aaagctatct   26940
atatatagct atctatgtct atatagctat ttttttaac ttcctttatt ttccttacag     27000
ggtttcagac aaaatcaaaa agaaggaagg tgctcacatt ccttaaatta aggagtaagt   27060
ctgccagcat tatgaaagtg aatcttactt ttgtaaaact ttatggtttg tggaaaacaa   27120
atgttttgga acatttaaaa agttcagatg ttaaaaagtt gaaaggttaa tgtaaaacaa   27180
tcaatattaa agaattttga tgccaaaact attagataaa aggttaatct acatccctac   27240
```

```
tagaattctc atacttaact ggttggttat gtggaagaaa catactttca caataaagag    27300
ctttaggata tgatgccatt ttatatcact agtaggcaga ccagcagact ttttttttatt   27360 gtgatatggg ataacctagg catactgcac tgtacactct gacatatgaa gtgctctagt    27420
caagtttaac tggtgtccac agaggacatg gtttaactgg aattcgtcaa gcctctggtt    27480
ctaatttctc atttgcagga aatgctggca tagagcagca ctaaatgaca ccactaaaga    27540
aacgatcaga cagatctgga atgtgaagcg ttatagaaga taactggcct catttcttca    27600
aaatatcaag tgttgggaaa gaaaaaagga agtggaatgg gtaactcttc ttgattaaaa    27660
gttatgtaat aaccaaatgc aatgtgaaat atttttactgg actctatttt gaaaaaccat   27720
ctgtaaaaga ctggggtggg ggtgggaggc cagcacggtg gtgaggcagt tgagaaaatt    27780
tgaatgtgga ttagattttg aatgatattg gataattatt ggtaatttta tgagctgtga    27840
gaagggtgtt gtagtttata aaagactgtc ttaatttgca tacttaagca tttaggaatg    27900
aagtgttaga gtgtcttaaa atgtttcaaa tggtttaaca aaatgtatgt gaggcgtatg    27960
tggcaaaatg ttacagaatc taactggtgg acatggctgt tcattgtact gttttttttct   28020 atcttctata tgtttaaaag tatataataa aaatatttaa tttttttta aa             28072
```

<210> SEQ ID NO 2
<211> LENGTH: 172
<212> TYPE: DNA
<213> ORGANISM: Homo sapiens

<400> SEQUENCE: 2

```
taaatgtcaa atttatgtat gggctgtgat tgaaacaaag acaccttaaa tgtcaaattt     60
atgtatggga acacacacac acacacacac acacacacac acacacacac acacacacac    120
atatatataa attttttacc tgagaagtta ggtgtctttg tttcaatcac ag            172
```

<210> SEQ ID NO 3
<211> LENGTH: 146
<212> TYPE: DNA
<213> ORGANISM: Homo sapiens

<400> SEQUENCE: 3

```
tccatggata cggagagctg tgatggcacc acaaccatgc tccatggata cggagagctg     60
actctgtgtg tgtgtgtgtg tgtgtgtgtg tgtgtgtgtg tgtgtgtgtg tatggcttca    120
tttcatgcat ggttgtggtg ccatca                                         146
```

<210> SEQ ID NO 4
<211> LENGTH: 236
<212> TYPE: DNA
<213> ORGANISM: Homo sapiens

<400> SEQUENCE: 4

```
tcaggaccct cctcatcatc cgggatctct tctccacaga tcaggaccct cctcatcatc     60 tcccttcat actgagtaga aatcagaggc ttgctttatt cttcaactac catttctatt    120
tccttcttcc aaaaccaggg tgaagcctct gaggggtgtg tgtgtgtgtg tgtgtgtgtg    180
tgtgtgtgtg tgtgtgtgtg tagatgaatg ctaaactctg tggagaagag atcccg       236
```

<210> SEQ ID NO 5
<211> LENGTH: 196
<212> TYPE: DNA
<213> ORGANISM: Homo sapiens

<400> SEQUENCE: 5

```
ggatctctga ggctgcacat gaaagtcttt gatgagatac cgggatctct gaggctgcac      60
atgtgcgtgc gcaaacacac acacacacac acacacacac acacacacac ccctccacac     120
ctttcttcct gctgcagtct gttgccttc aaaatctttt ccctcactta tttacggtat      180
ctcatcaaag actttc                                                     196
```

<210> SEQ ID NO 6
<211> LENGTH: 180
<212> TYPE: DNA
<213> ORGANISM: Homo sapiens

<400> SEQUENCE: 6

```
acacacatgc acgctctctc aagagcacag tttggagtga gagacacaca tgcacgctct      60
ctcagacatg atctgatgtc gcacacacac acacacacac acacacacac acacacacac     120
gattcaacaa ataagtgatg agttcaaaca tggggttctc tcactccaaa ctgtgctctt     180
```

<210> SEQ ID NO 7
<211> LENGTH: 170
<212> TYPE: DNA
<213> ORGANISM: Homo sapiens

<400> SEQUENCE: 7

```
ctaaaatctt ttgttaagct cctcctaaac tgaactttca aagctctaaa atcttttgtt      60
aagctcctcc agtgaatttt catttcagat actgtgtgtg tgtgtgtgtg tgtgtgtgtg     120
tgtgtgtacc aactgaatat atatattcag ctttgaaagt tcagtttagg                170
```

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8

```
ggatctctga ggctgcacat                                                  20
```

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9

```
gaaagtcttt gatgagatac                                                  20
```

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10

```
acacacatgc acgctctctc                                                  20
```

<210> SEQ ID NO 11
<211> LENGTH: 20
<212> TYPE: DNA
<213> ORGANISM: Artificial Sequence

```
<220> FEATURE:
<223> OTHER INFORMATION: Synthetic primer

<400> SEQUENCE: 11
aagagcacag tttggagtga                                        20

<210> SEQ ID NO 12
<211> LENGTH: 23
<212> TYPE: DNA
<213> ORGANISM: Artificial Sequence
<220> FEATURE:
<223> OTHER INFORMATION: Synthetic primer

<400> SEQUENCE: 12
taaatgtcaa atttatgtat ggg                                    23

<210> SEQ ID NO 13
<211> LENGTH: 23
<212> TYPE: DNA
<213> ORGANISM: Artificial Sequence
<220> FEATURE:
<223> OTHER INFORMATION: Synthetic primer

<400> SEQUENCE: 13
ctgtgattga aacaaagaca cct                                    23

<210> SEQ ID NO 14
<211> LENGTH: 23
<212> TYPE: DNA
<213> ORGANISM: Artificial Sequence
<220> FEATURE:
<223> OTHER INFORMATION: Synthetic primer

<400> SEQUENCE: 14
ctaaaatctt tgttaagct cct                                     23

<210> SEQ ID NO 15
<211> LENGTH: 22
<212> TYPE: DNA
<213> ORGANISM: Artificial Sequence
<220> FEATURE:
<223> OTHER INFORMATION: Synthetic primer

<400> SEQUENCE: 15
cctaaactga actttcaaag ct                                     22

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
tccatggata cggagagctg                                        20

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17
tgatggcacc acaaccatgc                                        20
```

```
<210> SEQ ID NO 18
<211> LENGTH: 20
<212> TYPE: DNA
<213> ORGANISM: Artificial Sequence
<220> FEATURE:
<223> OTHER INFORMATION: Synthetic primer

<400> SEQUENCE: 18
tcaggaccct cctcatcatc                                                    20

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
cgggatctct tctccacaga                                                    20

<210> SEQ ID NO 20
<211> LENGTH: 25
<212> TYPE: DNA
<213> ORGANISM: Artificial Sequence
<220> FEATURE:
<223> OTHER INFORMATION: Synthetic primer

<400> SEQUENCE: 20
tcctttattt tccttacagg gtttc                                              25

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
caatgaacag ccatgtccac                                                    20

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
aggaaatgct ggcatagagc                                                    20

<210> SEQ ID NO 23
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
ctgctctatg ccagcatttc                                                    20

<210> SEQ ID NO 24
<211> LENGTH: 22
<212> TYPE: DNA
<213> ORGANISM: Artificial Sequence
<220> FEATURE:
<223> OTHER INFORMATION: Synthetic primer
```

```
<400> SEQUENCE: 24
aaaagtctgc tggtctgcct ac                                          22
```